United States Patent
Dugar et al.

(10) Patent No.: US 9,556,156 B2
(45) Date of Patent: Jan. 31, 2017

(54) COMPOUNDS, THEIR SYNTHESIS AND THEIR USES

(71) Applicant: Sphaera Pharma Pte Ltd, Singapore (SG)

(72) Inventors: Sundeep Dugar, Haryana (IN); Frank Peter Hollinger, Haryana (IN); Dinesh Mahajan, Haryana (IN); Rhushikesh Chandrabhan Deokar, Haryana (IN)

(73) Assignee: SPHAERA PHARMA PTE LTD., Singapore (SG)

( * ) Notice: Subject to any disclaimer, the term of this patent is extended or adjusted under 35 U.S.C. 154(b) by 0 days.

(21) Appl. No.: 14/433,485

(22) PCT Filed: Oct. 7, 2013

(86) PCT No.: PCT/IN2013/000607
§ 371 (c)(1),
(2) Date: Apr. 3, 2015

(87) PCT Pub. No.: WO2014/054058
PCT Pub. Date: Apr. 10, 2014

(65) Prior Publication Data
US 2015/0252027 A1    Sep. 10, 2015

(30) Foreign Application Priority Data

Oct. 5, 2012  (IN) .......................... 3114/DEL/2012

(51) Int. Cl.
| | | |
|---|---|---|
| *C07D 405/14* | (2006.01) |
| *C07D 213/82* | (2006.01) |
| *C07D 401/14* | (2006.01) |
| *C07D 471/14* | (2006.01) |
| *C07D 487/04* | (2006.01) |

(52) U.S. Cl.
CPC ........... *C07D 405/14* (2013.01); *C07D 213/82* (2013.01); *C07D 401/14* (2013.01); *C07D 471/14* (2013.01); *C07D 487/04* (2013.01)

(58) Field of Classification Search
CPC .............................. C07D 405/14; C07D 213/82
See application file for complete search history.

(56) References Cited

U.S. PATENT DOCUMENTS

| | | | | |
|---|---|---|---|---|
| 5,525,727 A * | 6/1996 | Bodor | .............. | A61K 47/48161 546/39 |
| 6,028,085 A * | 2/2000 | Bromidge | ............ | C07D 401/12 514/333 |
| 9,079,928 B2 * | 7/2015 | Guenther | ................ | C07F 9/591 |

* cited by examiner

*Primary Examiner* — Golam M M Shameem

(74) *Attorney, Agent, or Firm* — Foley & Lardner LLP

(57) ABSTRACT

The present invention discloses novel chemical compounds obtained by causing a covalent attachment of a modifying agent of the structure provided for formula 1, to a functional group or a heteroatom of a heterocyclic ring system in chemical compound with improved chemical and biological properties. Wherein: Y is DRUG-CO; DRUG-OCO; DRUG-NRCO, and X is selected from.

4 Claims, No Drawings

US 9,556,156 B2

COMPOUNDS, THEIR SYNTHESIS AND THEIR USES

FIELD OF THE INVENTION

The present invention describes novel novel compounds and a method for the chemical modification of molecules, to alter their pharmacodynamic and pharmacokinetic properties.

BACKGROUND OF THE INVENTION

A chemical entity, which is potent in activity against its target, is the first step in the drug discovery process. However, a potent compound is only effective when an appropriate quantity is transported to the site of action at an acceptable rate after it has been administered. Even potent compounds benefit from optimization of these aspects. Many potent chemical entities do not have optimal pharmacokinetic parameters and hence the pharmacodynamic properties of these drugs are also suboptimal. In addition, there are several chemical entities that are already available in the market which have restricted pharmacokinetic properties and hence cannot be formulated in a manner convenient for patient administration.

The rate and extent of transportation into the blood circulation may be controlled by addition of certain groups to the original molecule, thereby modifying the molecule and its properties. Molecular modification is the chemical modification of a known and previously characterized lead compound for the purpose of enhancing its usefulness as a drug. This could mean enhancing its specificity for a particular target site, increasing its potency, improving its rate and extent of absorption, modifying the time course over which the active components become bio-available in the body (e.g., time release formulation), reducing its toxicity, and/or changing its physical or chemical properties (e.g., solubility) to optimize those aspects for particular applications.

However, the moiety used for molecular modification of the drug must be such that the therapeutic efficacy of the compound is retained and/or enhanced, while causing modification of the pharmacokinetic properties. Further, the novel compound, when administered, must not adversely affect the safety, toxicity and efficacy of the chemical entity beyond a tolerable degree.

Though there are certain methods to alter the pharmacokinetic profile of the compounds, which may or may not result in the alteration of the pharmacodynamic profiles, there are no methods available that are applicable to a wide range of drugs.

Hence there is a need for a novel method of modification of the drugs, which alter the pharmacokinetic and pharmacodynamic profile of the drugs.

DETAILED DESCRIPTION OF THE INVENTION

This invention provides novel chemical compounds, drugs or molecular entities that after chemical modification exhibit improved properties and are suitable for pharmaceutical use. The resultant novel compounds obtained by using the novel reagents of this invention are suitable for use as drugs and/or pharmaceutical agents with altered pharmacokinetic and/or pharmacodynamic profile(s), while maintaining a desirable safety and toxicity profile. The invention also provides a method for preparation of pharmaceutical agents and other biologically active substances more soluble in saline and/or at biologically useful pHs, a method to affect the pharmacokinetic properties of pharmaceutical agents and other biologically active substances, a method to affect the rate of conversion of the novel pharmaceutical agents and other biologically active substances to the original pharmaceutical agents and biologically active substances by modification of the chemical structure.

The chemical compounds on modification result in a change in the biological system and/or have an altered location(s) of conversion in the body of a warm blooded animal.

The present invention discloses a list of compounds that may be novel to have altered pharmacokinetic/pharmacodynamic profiles. The compounds that may be novel and as disclosed herein are selected from PCT/IN2012/000248. The compounds as disclosed herein, exhibit, surprising and advantageous properties, on chemical modification:

A. Novel Compounds of the Invention

The compounds selected from the classes as listed below may be novel as claimed in claim the method of this invention and the compounds on modification elicit altered pharmacodynamic and pharmacokinetic profiles.

Central Nervous System Drugs, such as CNS/Respiratory Stimulants, Analgesics, Narcotic Agonists, Narcotic agonist/antagonists, Nonsteroidal Anti-inflammatory/Analgesic Agents, Behavior-Modifying Agents, Tranquilizers/Sedatives, Anesthetic Agents, Inhalants, Narcotics, Reversal Agents, Anticonvulsants, Muscle Relaxants, Skeletal, Muscle Relaxants, Smooth, Euthanasia Agent, Cardiovascular Agents, Inotropic Agents, Antiarrhythmic Drugs, Anticholinergics, Vasodilating Agents, Agents Used in Treatment of Shock, Alpha-Adrenergic Blocking Agents, Beta-Adrenergic Blocking Agents, Respiratory Drugs, Bronchodilators, Sympathomimetics, Antihistamines, Antitussives, Renal and Urinary Tract, Agents for Urinary Incontinence/Retention, Urinary Alkalinizers, Urinary Acidifiers, Cholinergic Stimulants, Agents for Urolithiasis, Gastrointestinal Agents, Antiemetic Agents, Antacids, H2 Antagonists, Gastromucosal Protectants, Proton Pump Inhibitors, Appetite Stimulants, G1 Antispasmodics-Anticholinergics, G1 Stimulants, Laxatives, Saline, Bulk producing, Lubricant, Surfactant, Antidiarrheals, Hormones/Endocrine/Reproductive Agents, Sex Hormones, Anabolic steroids, Posterior Pituitary Hormones, Adrenal Cortical Steroids, Glucocorticoids, Antidiabetic Agents, Thyroid Drugs, Thyroid Hormones, Misc. Endocrine/Reproductive Drugs, Prostaglandins, Antiinfective Drugs, Antiparasitics, Anticoccidial Agents, Antibiotics, Anti-tuberculosis, Aminocyclitols, Cephalosporins, Macrolides, Penicillins, Tetracyclines, Lincosamides, Quinolones, Sulfonamides, Miscellaneous Antibacterials, Antifungal Agents, Antiviral Agents, Blood Modifying Agents, Clotting Agents, Anticoagulants, Erythropoietic Agents, Antineoplastics/Immunosuppresives, Alkylating Agents, Antidotes, Bone/Joint Agents, Dermatologic Agents (Systemic), Vitamins and Minerals/Nutrients, Systemic Acidifiers, Systemic Alkalinizers, anticancer agents, and anti-viral agents.

B. Method of Modifying the Compounds of the Present Invention

The present invention also discloses a method to modify the compounds so as to alter their pharmacokinetic and pharmacodynamic profiles. On altering the compounds as per the method of this invention, novel novel compounds of the present invention may be obtained.

The present invention disclosed novel chemical compounds obtained by causing a covalent attachment of a modifying agent of the structure provided for formula 1, to a functional group or a heteroatom of a heterocyclic ring system in chemical compound with improved chemical and biological properties;

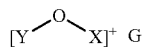

Wherein:
Y is DRUG-CO; DRUG-OCO; DRUG-NRCO, and
X is selected from

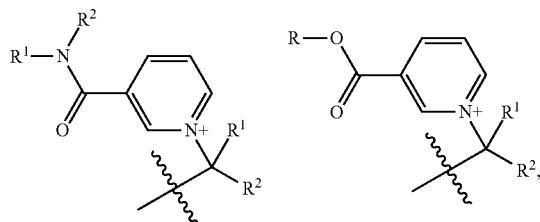

With a provisio that the modification can be done at more than one functional group in the DRUG.
Alternatively:
Y is DRUG-CR$^1$R$^2$, and
X is COR, CONRR$^2$, COOR
With a provisio that the N of the drug is attached to CR$^1$R$^2$.
With a provisio that the modification can be done at more than one functional group in the DRUG.

G$^-$ can be selected from iodide, chloride, bromide, mesylate, tosylate or tetra flouroborate or any other pharmaceutically acceptable anion. G$^-$ can be either one or more counter ions to balance the charge.

R, R$^1$ and R$^2$ are independently H, C$_1$-C$_8$ straight or branched chain alkyl—optionally containing 1-3 heteroatoms selected from O, N, S, SO, or SO$_2$; 3-7 membered cycloalkyl optionally containing 1-3 heteroatoms selected from O, N, S, SO, or SO$_2$ and or lower alkyl, straight or branched alkyl, alkoxy; alkaryl, aryl, heteroaryl, or alkheteroaryl; or is independently, is independently part of 3-7 membered ring optionally containing additional 1-2 heteroatoms selected from, O, N, S, SO, SO$_2$ and also be optionally substituted with alkoxy, F or Cl.

The method of modifying the compounds as per the present invention, involves, the step of causing a covalent attachment of a compound of formula 1, to a functional group or a heteroatom of a heterocyclic ring system to obtain a novel compound with improved chemical and biological properties.

The method for obtaining a novel chemical compound by causing a covalent attachment of a modifying agent of the structure provided for formula 1, to a functional group or a heteroatom of a heterocyclic ring system in chemical compound with improved chemical and biological properties; wherein

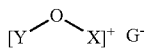

Wherein:
Y is DRUG-CO; DRUG-OCO; DRUG-NRCO, and
X is selected from

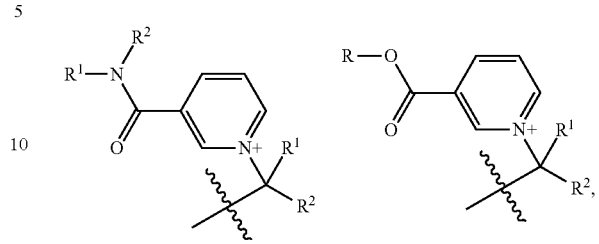

Alternatively:
Y is DRUG-CR$^1$R$^2$, and
X is COR, CONRR$^2$, COOR
With a provisio that the N of the drug is attached to CR$^1$R$^2$.
With a provisio that the modification can be done at more than one functional group in the DRUG.

G$^-$ can be selected from iodide, chloride, bromide, mesylate, tosylate or tetra flouroborate or any other pharmaceutically acceptable anion. G$^-$ can be either one or more counter ions to balance the charge.

R, R$^1$ and R$^2$ are independently H, C$_1$-C$_8$ straight or branched chain alkyl—optionally containing 1-3 heteroatoms selected from O, N, S, SO, or SO$_2$; 3-7 membered cycloalkyl optionally containing 1-3 heteroatoms selected from O, N, S, SO, or SO$_2$ and or lower alkyl, straight or branched alkyl, alkoxy; alkaryl, aryl, heteroaryl, or alkheteroaryl; or is independently is independently part of 3-7 membered ring optionally containing additional 1-2 heteroatoms selected from, O, N, S, SO, SO$_2$ and also be optionally substituted with alkoxy, F or Cl.

B.1 Compound of Formula (1)
The compounds of formula (1) may be represented as herein below:

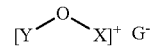

Wherein:
Y is DRUG-CO; DRUG-OCO; DRUG-NRCO, and
X is selected from

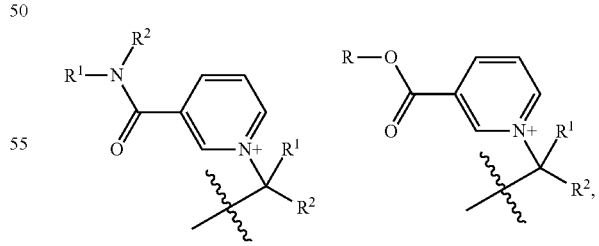

With a provisio that the modification can be done at more than one functional group in the DRUG.
Alternatively:
Y is DRUG-CR$^1$R$^2$, and
X is COR, CONRR$^1$, COOR
With a provisio that the N of the drug is attached to CR$^1$R$^2$.

With a provisio that the modification can be done at more than one functional group in the DRUG.

$G^-$ can be selected from iodide, chloride, bromide, mesylate, tosylate or tetra flouroborate or any other pharmaceutically acceptable anion. $G^-$ can be either one or more counter ions to balance the charge.

R, $R^1$ and R are independently H, $C_1$-$C_8$ straight or branched chain alkyl—optionally containing 1-3 heteroatoms selected from O, N, S, SO, or $SO_2$; 3-7 membered cycloalkyl optionally containing 1-3 heteroatoms selected from O, N, S, SO, or $SO_2$ and or lower alkyl, straight or branched alkyl, alkoxy; alkaryl, aryl, heteroaryl, or alkheteroaryl; or is independently is independently part of 3-7 membered ring optionally containing additional 1-2 heteroatoms selected from, O, N, S, SO, $SO_2$ and also be optionally substituted with alkoxy, F or Cl.

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g. methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. In preferred embodiments, a straight chain or branched chain alkenyl has 1-12 carbons in its backbone, preferably 1-8 carbons in its backbone, and more preferably 1-6 carbons in its backbone. Exemplary alkenyl groups include allyl, propenyl, butenyl, 2-methyl-2-butenyl, and the like.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. In preferred embodiments, an alkynyl has 1-12 carbons in its backbone, preferably 1-8 carbons in its backbone, and more preferably 1-6 carbons in its backbone. Exemplary alkynyl groups include propynyl, butynyl, 3-methylpent-1-ynyl, and the like.

The term alkoxy refers to an alkyl group singly bonded to oxygen.

The term "aralkyl", as used herein, refers to an alkyl group substituted with one or more aryl groups.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, naphthyl, biphenyl, anthracenyl and the like.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The terms "cycloalkyl" and "cycloalkenyl" refer to cyclic hydrocarbon groups of 3 to 12 carbon atoms.

The terms "halogen", "halide" and "halo", as used herein, mean halogen and include fluoro, chloro, bromo and iodo.

The term "unsaturated ring" includes partially unsaturated and aromatic rings.

The terms "heterocyclyl", "heterocycle", "heterocyclo" and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The heterocyclic group may be attached at any heteroatom or carbon atom of the ring or ring system. Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like. Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like. Exemplary tricyclic heterocyclic groups include carbazolyl, benzidolyl, phenanthrolinyl, acridinyl, phenanthridinyl, xanthenyl and the like.

The term "heteroalkyl", as used herein, refers to a saturated or unsaturated chain of carbon atoms including at least one heteroatom (e.g., O, S, or $NR^4$, such as where $R^4$ is H or lower alkyl).

The term "heteroaryl" includes substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The term "heteroaryl" also includes polycyclic ring systems having two or more cyclic rings in which two or more carbons are common to two adjoining rings wherein at least one of the rings is heteroaromatic, e.g., the other cyclic rings may be cycloalkyls, cycloalkenyls, cycloalkynyls, aryls, heteroaryls, and/or heterocyclyls. Preferred polycyclic ring systems have two cyclic rings in which both of the rings are aromatic. Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, quinolinyl, pyridazinyl, triazolyl, triazinyl, and the like.

The term "alkylene" in this text include both linear and branched, saturated and unsaturated (i.e. containing one double bond) divalent alkylene groups and monovalent alkyl groups, respectively.

The term "alkanol" in this text likewise includes linear and branched, saturated and unsaturated alkyl components of the alkanol groups, in which the hydroxyl groups may be situated at any position on the alkyl moiety. The term "cycloalkanol" includes unsubstituted or substituted (e.g. methyl or ethyl) cyclic alcohols.

The term "alkoxy" is intended to mean a alkyl radical, as defined herein, attached directly to an oxygen atom. Some embodiments are 1 to 5 carbons, some embodiments are 1 to 4 carbons, some embodiments are 1 to 3 carbons and some embodiments are 1 or 2 carbons. Examples include methoxy, ethoxy, n-propoxy, isopropoxy, n-butoxy, tert-butoxy, 5-isobutoxy, sec-butoxy, and the like.

The term "heteroatom", as used herein, means an atom of any element other than carbon or hydrogen. Preferred heteroatoms are nitrogen, oxygen, and sulfur.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents may be one or more and the same or different for appropriate organic compounds. For purposes of the invention, the heteroatoms such as nitrogen may have hydrogen substituents and/or any permissible substituents of organic compounds described herein which satisfy the valences of the heteroatoms.

The process of converting a tertiary amine into a quaternary ammonium compound is referred to as quaternization and the agents which are used in the above process are known as "Quaternizing Agents"

Pharmaceutical agents include any substance or agent considered to be a medicine, drug, or pharmaceutical agent.

Biologically active substances include any substance which exhibits a biological activity as understood by one skilled in the art.

Chemical and biological properties include pharmacokinetic and pharmacodynamic properties.

In another preferred embodiment, the present invention includes a method of using these novel derivatizing agents to modify one or more of the physicochemical and pharmacokinetic, and pharmacodynamic properties of pharmaceutical compounds. As the examples shown herein demonstrate, the method of the present invention may readily be applied to a wide variety of compounds to modify their properties in desirable ways.

Pharmaceutical agents include any substance or agent considered to be a medicine, drug, or pharmaceutical agent.

Biologically active substances include any substance which exhibits a biological activity as understood by one skilled in the art.

Chemical and biological properties include pharmacokinetic and pharmacodynamic properties.

In another preferred embodiment, the present invention includes a method of using these novel derivatizing agents to modify one or more of the physicochemical and pharmacokinetic, and pharmacodynamic properties of pharmaceutical compounds. As the examples shown herein demonstrate, the method of the present invention may readily be applied to a wide variety of compounds to modify their properties in desirable ways.

B.3. General Synthetic Schemes

The general synthetic schemes of the compounds are provided below as a means of illustration. In the schemes below, $R^x$, $R^y$ is H or alkyl and $R^1$ or $R^2$ are as defined above.

Scheme 1: Compounds with nitrogen-containing heterocycles such as pyridine, imidazole, triazole, etc.

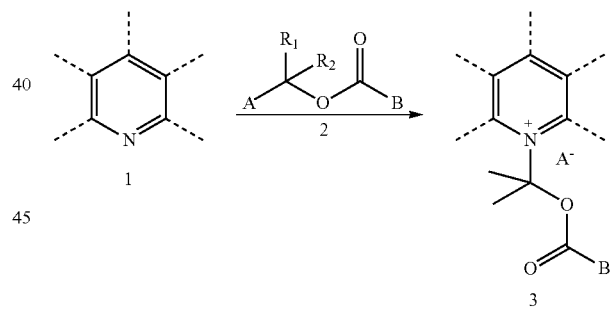

Any compound of biological importance with an aromatic nitrogen such as pyridine can be reacted with a desired methyl formyl reagent (Type I (B=R) or Type II (B=NR$^1$R$^2$) or Type III (B=OR) in a solvent such as acetonitrile/tetrahydrofuran/dichloromethane at temperatures typically ranging from ambient to 60° C., under anydrous conditions. After completion, the reaction can be concentrated by evaporating excess of organic solvent to get the desired product, which can be purified if required by any general purification method practiced in organic chemistry laboratory such as crystallization or preparative column purification.

Scheme 2: Modification of drugs/biologically active molecules containing aliphatic tertiary amines such as piperidine, piperazine and trialkyl amines.

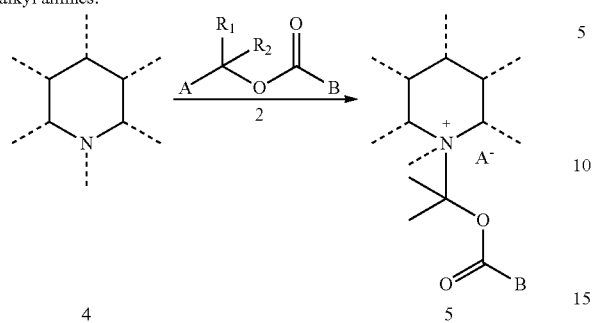

Any drug or molecule of biological importance having an aliphatic tertiary nitrogen such as piperidine can be reacted with a desired methyl formyl reagent (Type I (B=R) or Type II (B=NR$^1$R$^2$) or Type III (B=OR) in a solvent such as acetonitrile/tetrahydrofuran/dichloromethane at temperatures typically ranging from ambient to 60° C., under anydrous conditions. After completion, the reaction can be concentrated by evaporating excess of organic solvent to get the desired product, which can be purified if required by any general purification method practiced in organic chemistry laboratory such as crystallization or preparative column purification.

Drugs or biologically active molecules with alcohols and/or phenols and/or amines, both primary and secondary can also be reacted with a desired methyl formyl reagent followed by making a quaternary ammonium cation using amines such as pyridine, for example nicotinamide is a preferred embodiment. Non-limiting examples of such conversions with drugs or biologically active molecules are shown in Scheme 3.

Scheme 3:

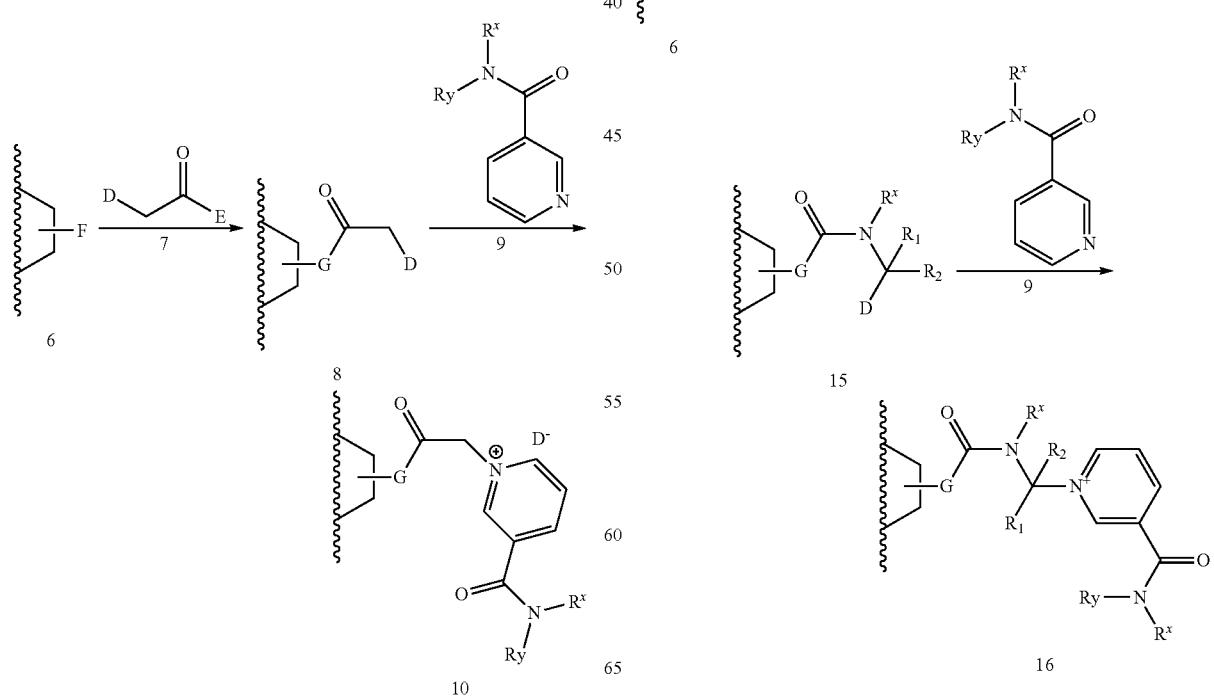

Wherein, F=OH, NH2 or NHR; G=O, NH or NR; $R^x/R^y$=H or alkyl or can be joined together to form a 3-6 membered ring;

Hence, drugs or biological active molecules with a primary or secondary amino group [6] can be reacted with a desired methyl formyl reagent in a solvent such as acetonitrile/tetrahydrofuran/dichloromethaneat temperatures typically ranging from ambient to 60° C., under anydrous conditions. After completion, the reaction can be concentrated by evaporating excess of organic solvent to get the desired product, which can be purified if required by any general purification method practiced in organic chemistry laboratory such as crystallization or preparative column purification By using the same procedure mentioned in scheme 3 the following chemical moieties containing phenolic groups are novel are compounds number 1001, 1002, 1003, 1004, 1005, 1006, 1007.

Scheme 4: Chemical moiety containing Amide (CONHR) as functional group

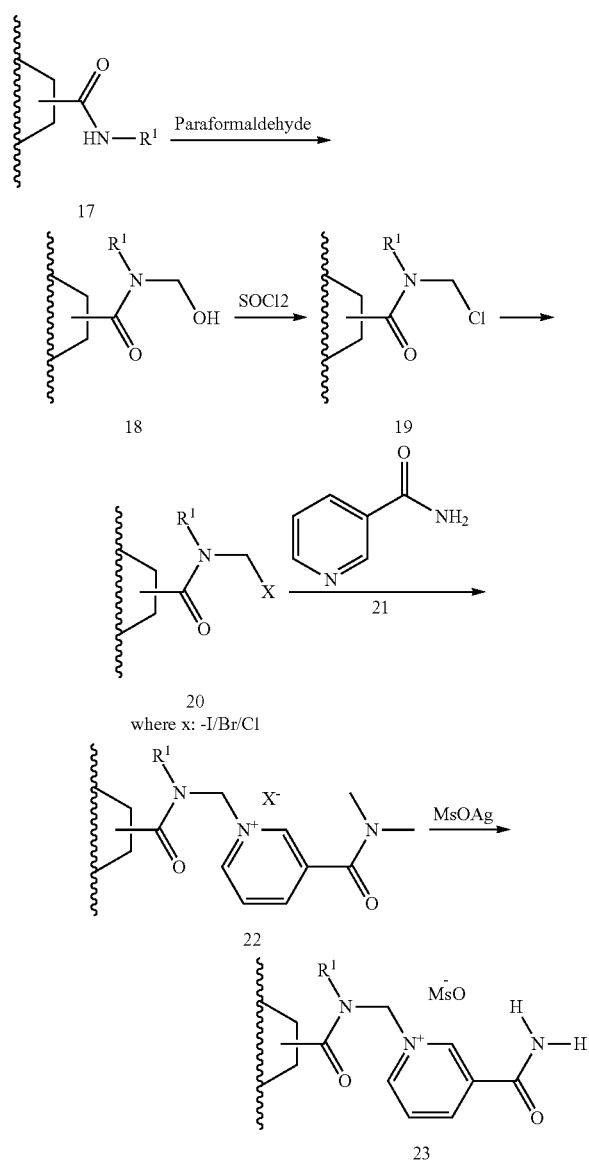

Drugs or biological active molecules with an amide group [17] can be reacted with paraformaldehyde at refluxing condition to yield precipitate of intermediate [18] which was filtered and dried. This resulting intermediate was converted to corresponding chloromethyl derivative [19] by using reagent such as thionyl chloride in solvent such as DMF, which can be further reacted with nicotinamide [20] as such or by converting it into respective bromo methyl or iodo methyl derivative using metal halides such as sodium iodide in solvent such as acetone or DCM or ACN at room temperature to refluxing. On standard work up resulted into corresponding iodo quat [21] which on further treatment with silver salts such as silver mesylate in solvent such as acetonitrile yield the desired final novel drug or biological active molecule [22].

Scheme 5: Chemical moiety containing Amide (CONHR) as functional group

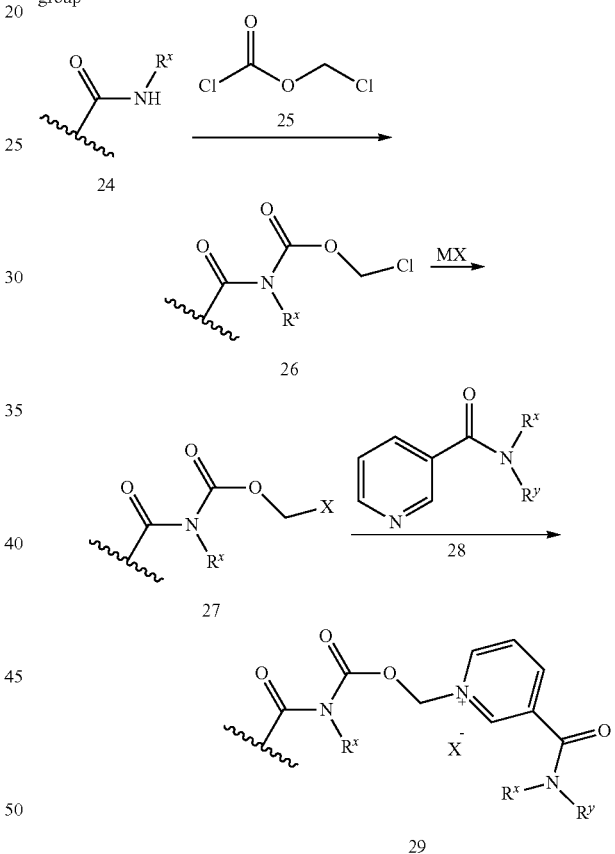

Drugs or biological active molecules containing amide such as [24] can be reacted with chloromethyl chloroformate [25] in presence of a base such as pyridine and a solvent such as DCM. Standard workup of the reaction mixture yields an intermediate [26]. This intermediate on reaction with a suitable metal salt such as sodium iodide in a solvent such as acetone at a desired temperature starting from ambient to heating followed by a standard workup yields compound [27]. Compound [27] on reaction with a suitable quaternization reagent such as nicotinamide [28] using solvent such as DCM at room temperature followed by evaporation of organic solvent provides the desired novel drug or biological active molecule [29].

Scheme 6: Modification of drugs/biologically active molecules with a carboxylic acid moiety

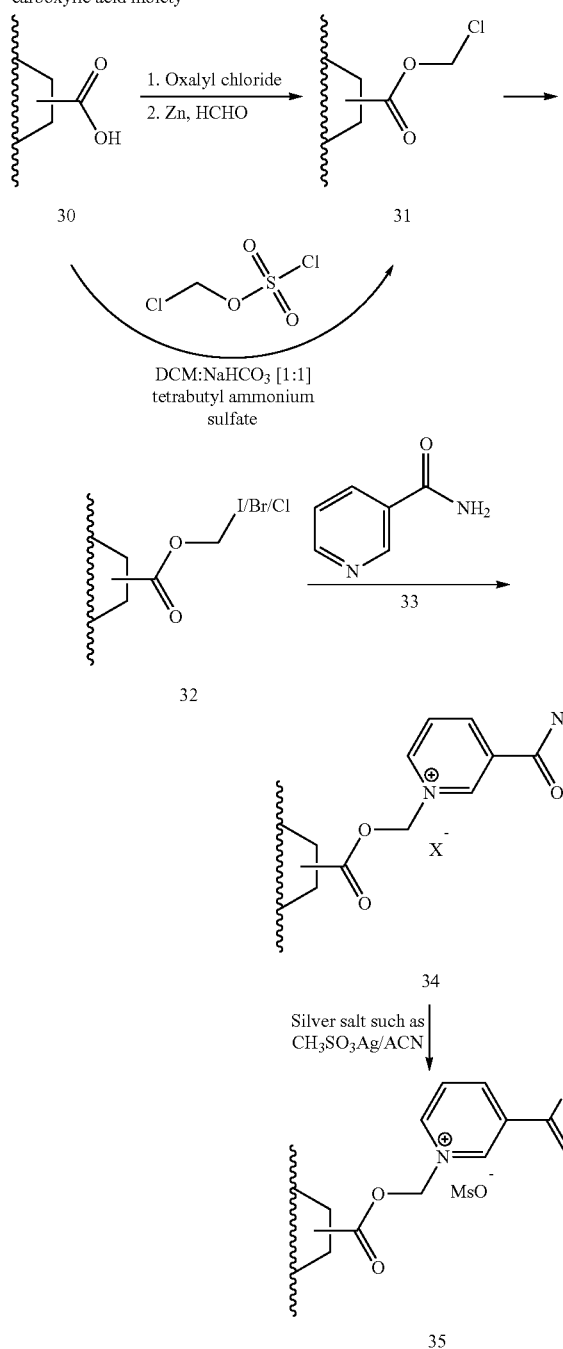

Scheme 7: Chemical moiety containing COOH as functional groups

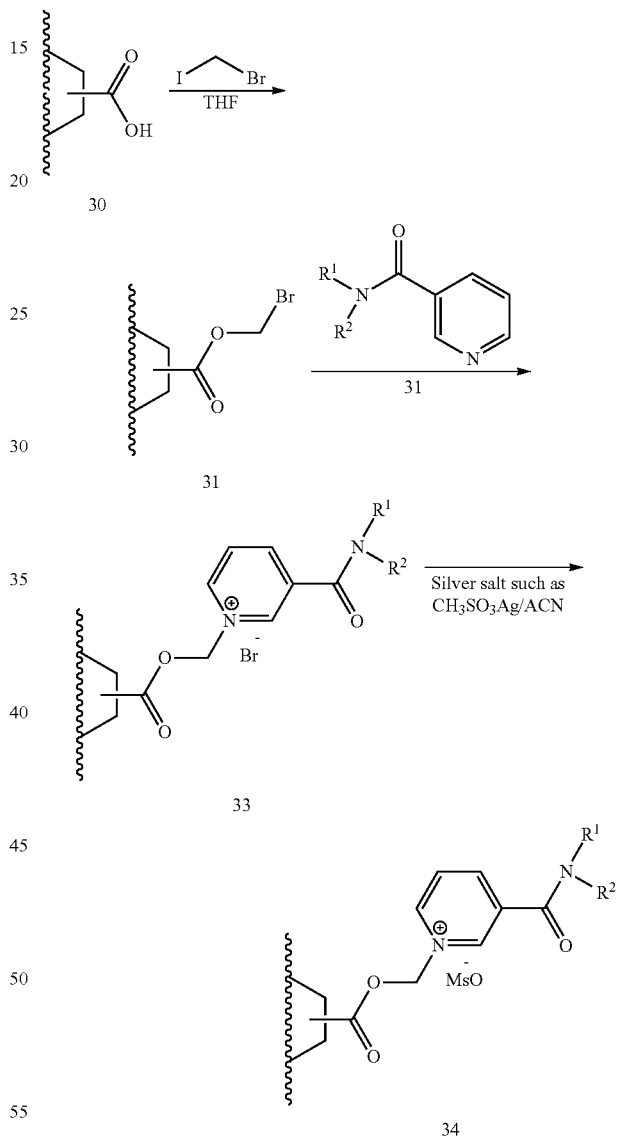

In a similar fashion, the corresponding drug or biological active molecule with a carboxylic acid group [30] may be reacted with Lewis acids such as zinc chloride (dry) and aldehydes such as paraformaldehyde at temperatures ranging from −10° C. to 60° C. for a time ranging up to 20-24 hours. Standard work up of the reaction mixture yields the intermediate [31]; alternatively, the corresponding drug or biological active molecule with a carboxylic acid group [30] dichloromethane may also be treated with a base such as sodium bicarbonate and tetrabutylammonium bisulfate followed by dropwise addition of chloromethyl chlorosulfate in solvent such as dichloromethane. On completion of the reaction, the organic layer was washed with aqueous $Na_2CO_3$ followed by standard work up and purifications, yields intermediate [31], which may be further reacted with nicotinamide [33] as such or by converting it into respective bromo methyl or iodo methyl [32] derivative using metal halides such as sodium iodide in solvent such as acetone or DCM or ACN at room temperature. On standard work up resulted into corresponding iodo quat [34] which on further treatment with silver salts such as silver mesylate in solvent such as acetonitrile yield the desired final novel drug or biological active molecule [34] or [35].

In a similar fashion, the corresponding drug or biological active molecule with a carboxylic acid group [63] may be reacted with a base such as cesium carbonate followed by the addition of a reagent such as bromo iodomethane in a solvent such as THF. On completion of the reaction followed by standard work up and purifications, yield substituted methyl formyl reagents, [78], which may be further reacted with a quaternization reagent such as nicotinamide [30] in a solvent such as ACN. The reaction mixture on evaporation yields desired products [79] which on further treatment with silver salts such as silver mesylate in solvent such as acetonitrile yield the desired final novel drug or biological active molecule [80].

By using the same procedure mentioned in Scheme 12 the following Chemical moieties containing acid groups are novel as, 1008, 1010, 1011, 1012, 1014, 1015, 1016, 1018, 1019, 1020, 1021, 1022.

C. Certain Novel Compounds of the Present Invention

Certain compounds, illustrative of the present invention are presented at Table 1

TABLE 1

Illustrative compounds of the present invention

| No. | IUPAC name | Structure |
|---|---|---|
| 1001 | 1-(((2,6-diisopropylphenoxy)carbonyloxy)methyl)-3-(dimethylcarbamoyl)pyridinium mesylate | 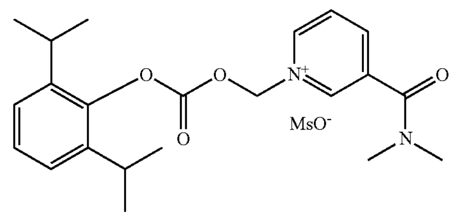 [SMILES: "MsO-" ; CC(C)c1cccc(C(C)C)c1OC(=O)OC[n+]1cccc(C(=O)N(C)C)c1] |
| 1002 | 1-(((2,6-diisopropylphenoxy)carbonyloxy)methyl)-3-(methylcarbamoyl)pyridinium mesylate | 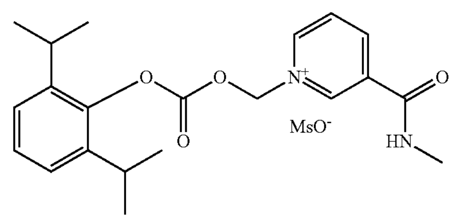 [SMILES: "MsO-" ; CNC(=O)c1ccc[n+](COC(=O)Oc2c(C(C)C)cccc2C(C)C)c1] |
| 1003 | 3-carbamoyl-1-(((2,6-diisopropylphenoxy)carbonyloxy)methyl) pyridinium mesylate | 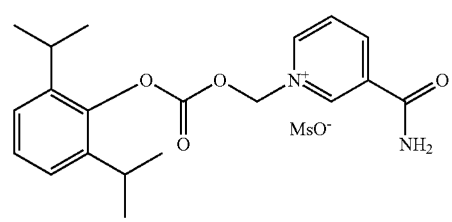 [SMILES: "MsO-" ; CC(C)c1cccc(C(C)C)c1OC(=O)OC[n+]1cccc(C(N)=O)c1] |
| 1004 | 1-(((2,6-diisopropylphenoxy)carbonyloxy)methyl)-3-(methylcarbamoyl)pyridinium iodide | 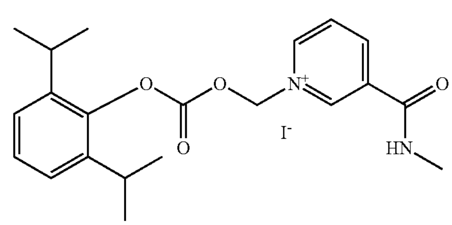 [SMILES: CNC(=O)c1ccc[n+](COC(=O)Oc2c(C(C)C)cccc2C(C)C)c1 ; [I-]] |
| 1005 | (E)-3-(dimethylcarbamoyl)-1-(((2-methoxy-4-((8-methylnon-6-enamido)methyl)phenoxy)carbonyloxy)methyl) pyridinium mesylate | 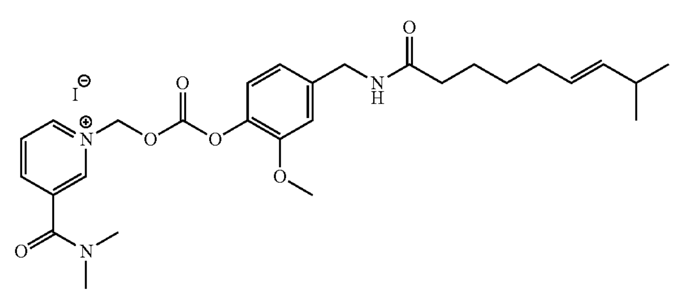 [SMILES: COc1cc(CNC(=O)CCCC/C=C/C(C)C)ccc1OC(=O)OC[n+]1cccc(C(=O)N(C)C)c1 ; [I-]] |

TABLE 1-continued

Illustrative compounds of the present invention

| No. | IUPAC name | Structure |
|---|---|---|
| 1006 | (E)-3-(dimethylcarbamoyl)-1-(((2-methoxy-4-((8-methylnon-6-enamido)methyl)phenoxy)carbonyloxy)methyl)pyridinium mesylate | 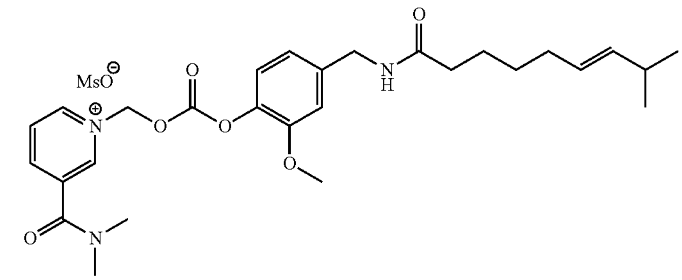 [SMILES: "MsO" ; COc1cc(CNC(=O)CCCC/C=C/C(C)C)ccc1OC(=O)OC[n+]1cccc(C(=O)N(C)C)c1] |
| 1007 | 3-(dimethylamino)-1-(((4-((1E,4Z,6E)-5-hydroxy-7-(4-hydroxy-3-methoxyphenyl)-3-oxohepta-1,4,6-trienyl)-2-methoxyphenoxy)carbonyloxy)methyl)pyridinium iodide | 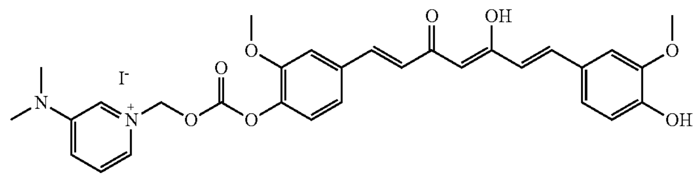 |
| 1008 | 3-(dimethylcarbamoyl)-1-((2-(4-isobutylphenyl)propanoyloxy)methyl)pyridinium iodide | 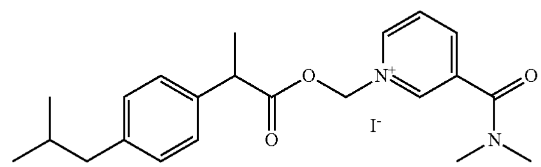 [SMILES: CC(C)Cc1ccc(C(C)C(=O)OC[n+]2cccc(C(=O)N(C)C)c2)cc1 ; [I-]] |
| 1009 | | 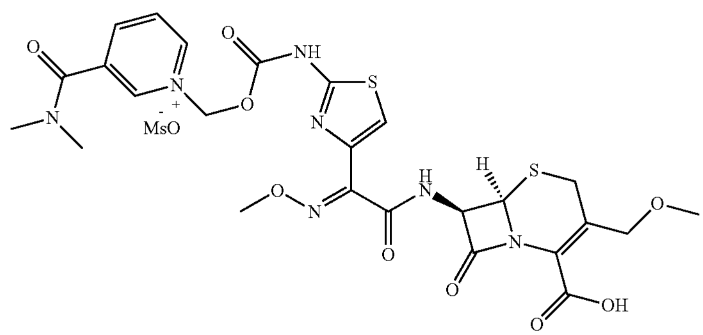 |
| 1010 | 1-((2-acetoxybenzoyloxy)methyl)-3-carbamoylpyridinium iodide | 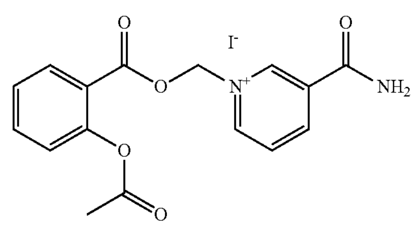 [SMILES: CC(=O)Oc1ccccc1C(=O)OC[n+]1cccc(C(N)=O)c1 ; [I-]] |
| 1011 | 1-((2-acetoxybenzoyloxy)methyl)-3-(methylcarbamoyl)pyridinium iodide | 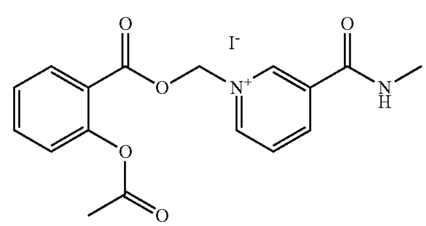 [SMILES: CNC(=O)c1ccc[n+](COC(=O)c2ccccc2OC(C)=O)c1 ; [I-]] |

TABLE 1-continued

Illustrative compounds of the present invention

| No. | IUPAC name | Structure |
|---|---|---|
| 1012 | 1-((2-acetoxybenzoyloxy)methyl)-3-(dimethylcarbamoyl)pyridinium iodide | 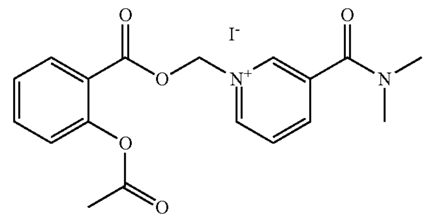 [SMILES: CC(=O)Oc1ccccc1C(=O)OC[n+]1cccc(C(=O)N(C)C)c1 ; [I-]] |
| 1013 | 1-((2-acetoxybenzoyloxy)methyl)-3-carbamoylpyridiniummesylate | 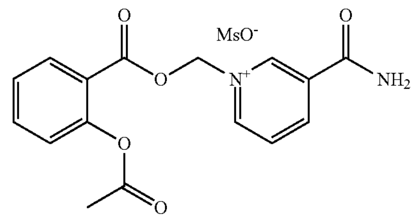 [SMILES: "MsO-" ; CC(=O)Oc1ccccc1C(=O)OC[n+]1cccc(C(N)=O)c1] |
| 1014 | 1-((2-acetoxybenzoyloxy)methyl)-3-(dimethylcarbamoyl)pyridiniummesylate | 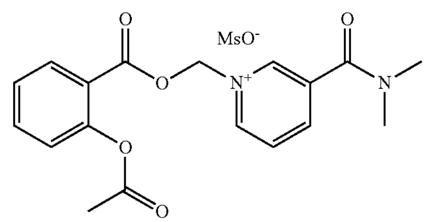 [SMILES: "MsO-" ; CC(=O)Oc1ccccc1C(=O)OC[n+]1cccc(C(=O)N(C)C)c1] |
| 1015 | 1-((2-acetoxybenzoyloxy)methyl)-3-(methylcarbamoyl)pyridinium mesylate | 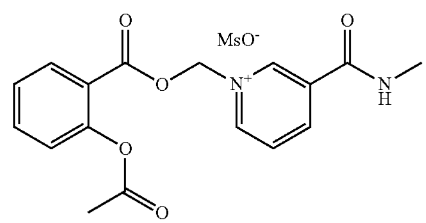 [SMILES: "MsO-" ; CNC(=O)c1ccc[n+](COC(=O)c2ccccc2OC(C)=O)c1] |
| 1016 | | 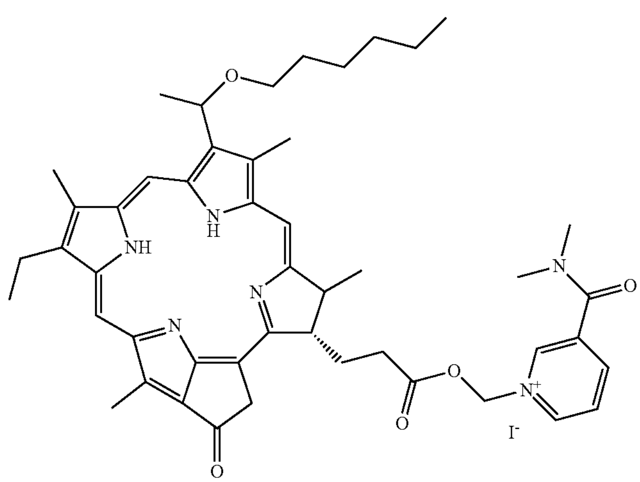 [SMILES: CCCCCCOC(C)c1c(C)c2cc3nc(c4c5nc(cc6[nH]c(cc1[nH]2)c(C)c6CC)C(C)=C5C(=O)C4)[C@@H](CCC(=O)OC[n+]1cccc(C(=O)N(C)C)c1)C3C ; [I-]] |

TABLE 1-continued

Illustrative compounds of the present invention

| No. | IUPAC name | Structure |
|-----|------------|-----------|
| 1017 | | 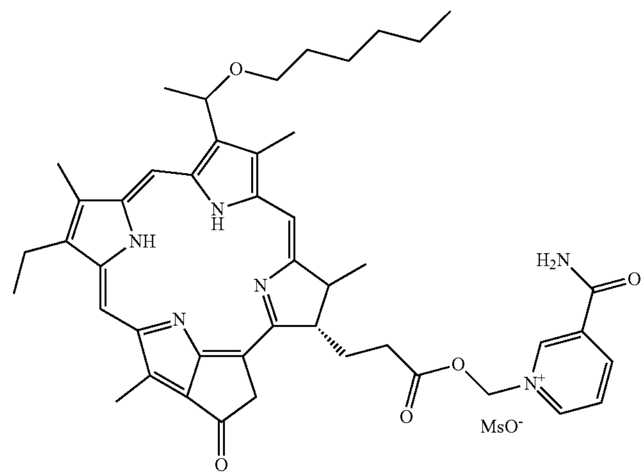 [SMILES: CCCCCCOC(C)c1c(C)c2cc3nc(c4c5nc(cc6[nH]c(cc1[nH]2)c(C)c6CC)C(C)=C5C(=O)C4)[C@@H](CCC(=O)OC[n+]1cccc(C(N)=O)c1)C3C ; "MsO-"] |
| 1018 | 3-carbamoyl-1-((2-(1-(4-chlorobenzoyl)-5-methoxy-2-methyl-1H-indol-3-yl)acetoxy)methyl)pyridinium iodide | 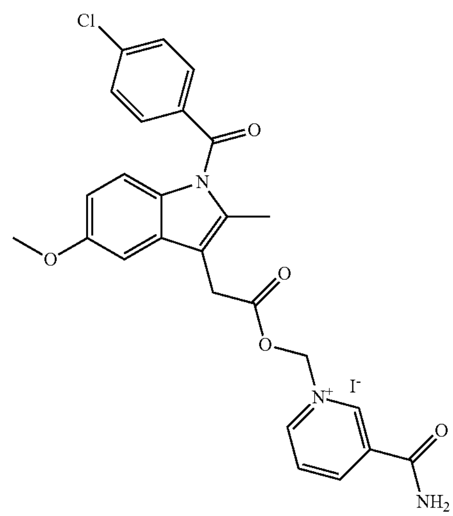 [SMILES: COc1ccc2c(c1)c(CC(=O)OC[n+]1cccc(C(N)=O)c1)c(C)n2C(=O)c1ccc(Cl)cc1 ; [I-]] |
| 1019 | 1-((2-(1-(4-chlorobenzoyl)-5-methoxy-2-methyl-1H-indol-3-yl)acetoxy)methyl)-3-(dimethylcarbamoyl)pyridinium iodide | 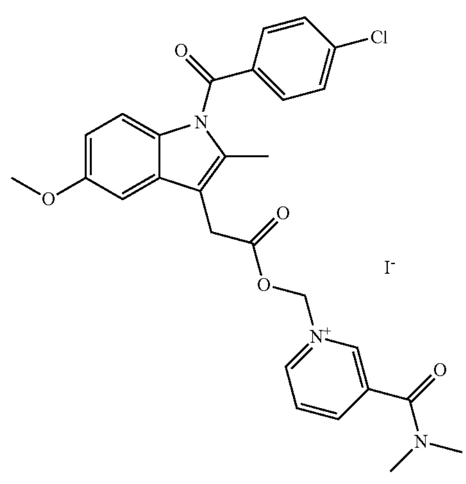 |

TABLE 1-continued

Illustrative compounds of the present invention

| No. | IUPAC name | Structure |
|---|---|---|
| 1020 | 1-((2-(1-(4-chlorobenzoyl)-5-methoxy-2-methyl-1H-indol-3-yl)acetoxy)methyl)-3-(dimethylcarbamoyl)pyridinium mesylate | 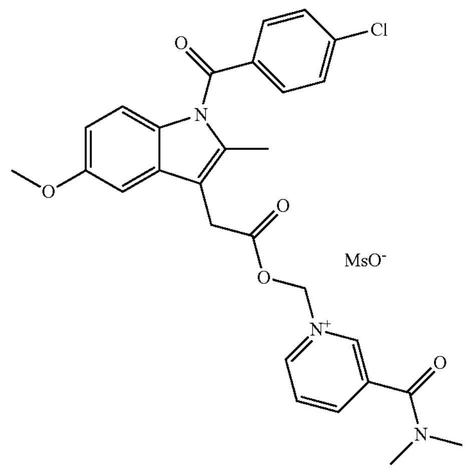 |
| 1021 | 1-((2-(2-(2,6-dichlorophenylamino)phenyl)acetoxy)methyl)-3-(dimethylcarbamoyl)pyridinium iodide | 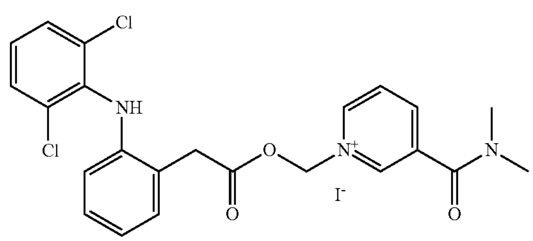 [SMILES: CN(C)C(=O)c1ccc[n+](COC(=O)Cc2ccccc2Nc2c(Cl)cccc2Cl)c1 ; [I-]] |
| 1022 | 1-(2-(4-acetamidophenoxy)-2-oxoethyl)-3-(dimethylcarbamoyl)pyridin-1-ium iodide | 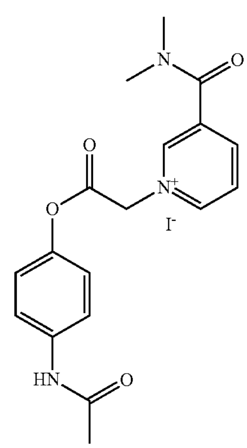 [SMILES: CC(=O)Nc1ccc(OC(=O)C[n+]2cccc(C(=O)N(C)C)c2)cc1 ; [I-]] |

TABLE 1-continued

Illustrative compounds of the present invention

| No. | IUPAC name | Structure |
|---|---|---|
| 1023 | 1-((((((1S,2R)-1-benzamido-3-(((2aR,4S,4aS,6R,9S,11S,12S,12aR,12bS)-6,12b-diacetoxy-12-(benzoyloxy)-4-((((3-(dimethylcarbamoyl)pyridin-1-ium-1-yl)methoxy)carbonyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium diiodide | 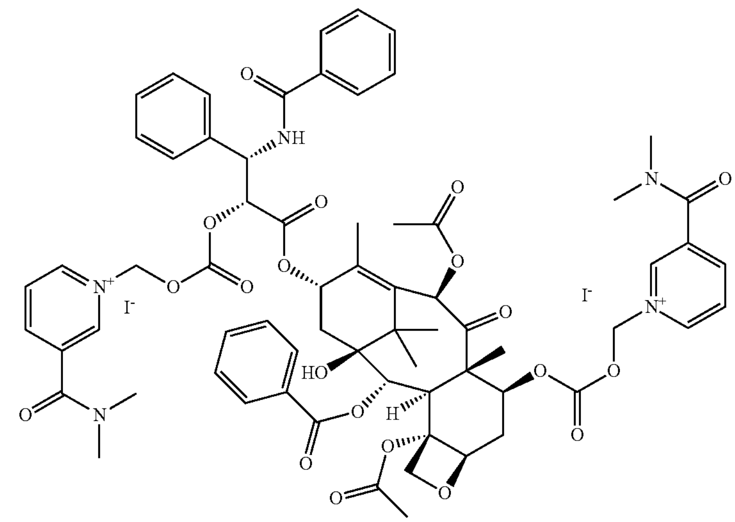 [SMILES: CC(=O)O[C@H]1C(=O)[C@]2(C)[C@@H](OC(=O)OC[n+]3cccc(C(=O)N(C)C)c3)C[C@H]3OC[C@@]3(OC(C)=O)[C@H]2[C@H](OC(=O)c2ccccc2)[C@]2(O)C[C@H](OC(=O)[C@H](OC(=O)OC[n+]3cccc(C(=O)N(C)C)c3)[C@@H](NC(=O)c3ccccc3)c3ccccc3)C(C)=C1C2(C)C ; [I-] ; [I-]] |
| 1024 | 1-((((6R,7R)-7-((E)-2-(2-aminothiazol-4-yl)-2-(methoxyimino)acetamido)-3-(methoxymethyl)-8-oxo-5-thia-1-azabicyclo[4.2.0]oct-2-ene-2-carbonyl)oxy)methyl)-3-(dimethylcarbamoyl)pyridin-1-ium methane sulfonate | 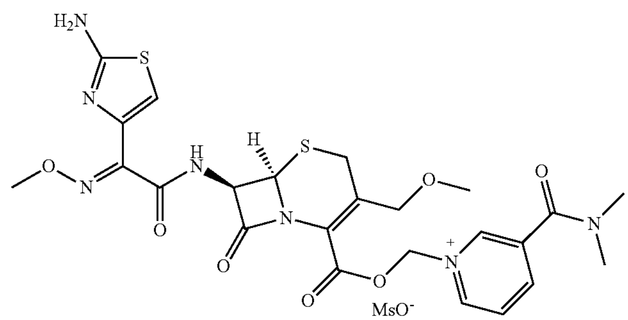 |
| 1025 | L(S)-1-((2-(carboxymethyl)-4-methylpentylcarbamoyloxy)methyl)-3-(dimethylcatbamoyl)pyridinium methanesulfonate | 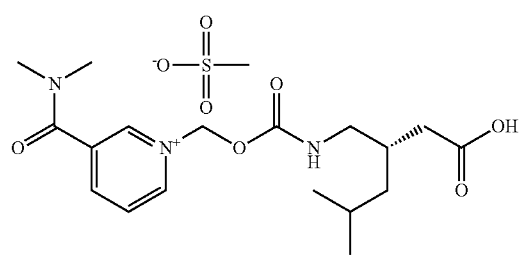 |
| 1026 | (S)-1-((2-(carboxymethyl)-4-methylpentylcarbamoyloxy)methyl)-3-(dimethylcarbamoyl)pyridinium iodide | 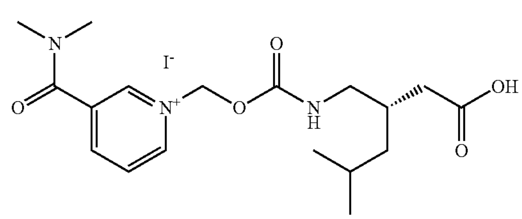 [SMILES: CC(C)C[C@H](CNC(=O)OC[n+]1cccc(C(=O)N(C)C)c1)CC(=O)O ; [I-]] |
| 1027 | 1-((2-((E)-1-(2-aminothiazol-4-yl)-2-((1S,8R)-5-(((3-(dimethylcarbamoyl)pyridinium-1-yl)methoxy)carbonyl)-7-oxo-4-vinyl-2-thiabicyclo[4.2.0]oct-4-en-8-ylamino)-2-oxoethylideneaminooxy)acetoxy)methyl)-3-(dimethylcarbamoyl)pyridinium | 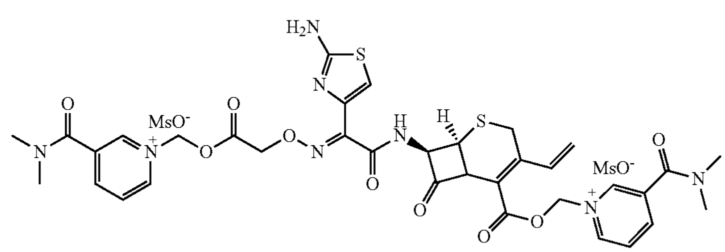 |

TABLE 1-continued

Illustrative compounds of the present invention

| No. | IUPAC name |
|---|---|
| 1028 | 1-((2-((E)-1-(2-aminothiazol-4-yl)-2-((1S,8R)-5-(((3-(dimethylcarbamoyl)pyridinium-1-yl)methoxy)carbonyl)-7-oxo-4-vinyl-2-thiabicyclo[4.2.0]oct-4-en-8-ylamino)-2-oxoethylideneaminooxy)acetoxy)methyl)-3-(dimethylcarbamoyl)pyridinium |
| 1029 | 1-((4-((E)-2-((6R,7R)-2-carboxy-8-oxo-3-vinyl-5-thia-1-azabicyclo[4.2.0]oct-2-en-7-ylamino)-1-(carboxymethoxyimino)-2-oxoethyl)thiazol-2-ylcarbamoyloxy)methyl)-3-(dimethylcarbamoyl)pyridinium |
| 1030 | 1-((((2,6-diisopropylphenoxy)carbonyl)oxy)methyl)-3-(dimethylcarbamoyl)pyridin-1-ium iodide |
| 1031 | 3-carbamoyl-1-((((2,6-diisopropylphenoxy)carbonyl)oxy)methyl)pyridin-1-ium iodide |

TABLE 1-continued

Illustrative compounds of the present invention

| No. | IUPAC name |
|---|---|
| 1032 | 1-(((isopropylcarbamoyl)oxy)methyl)-3-(2-((2-methyl-5-((3-(4-methyl-1H-imidazol-3-ium-1-yl)-5-(trifluoromethyl)phenyl)carbamoyl)phenyl)amino)pyrimidin-4-yl)pyridin-1-ium methanesulfonate |
| 1033 | 1-(((isopropoxycarbonyl)oxy)methyl)-3-(2-((2-methyl-5-((3-(4-methyl-1H-imidazol-3-ium-1-yl)-5-(trifluoromethyl)phenyl)carbamoyl)phenyl)amino)pyrimidin-4-yl)pyridin-1-ium methanesulfonate |
| 1034 | 3-(2-((2-methyl-5-((3-(4-methyl-1H-imidazol-3-ium-1-yl)-5-(trifluoromethyl)phenyl)carbamoyl)phenyl)amino)pyrimidin-4-yl)-1-((2-phenylacetoxy)methyl)pyridin-1-ium methanesulfonate |
| 1035 | 1-((isobutyryloxy)methyl)-3-(2-((2-methyl-5-((3-(4-methyl-1H-imidazol-3-ium-1-yl)-5-(trifluoromethyl)phenyl)carbamoyl)phenyl)amino)pyrimidin-4-yl)pyridin-1-ium methanesulfonate |
| 1036 | 4-((4-ethoxy-3-(1-methyl-7-oxo-3-propyl-4,7-dihydro-1H-pyrazolo[4,3-d]pyrimidin-5-yl)phenyl)sulfonyl)-1-((isobutyryloxy)methyl)-1-methylpiperazin-1-ium iodide |

TABLE 1-continued

Illustrative compounds of the present invention

| No. | IUPAC name | Structure |
|-----|------------|-----------|
| 1037 | 4-((4-ethoxy-3-(1-methyl-7-oxo-3-propyl-4,7-dihydro-1H-pyrazolo[4,3-d]pyrimidin-5-yl)phenyl)sulfonyl)-1-((isobutyryloxy)methyl)-1-methylpiperazin-1-ium methanesulfonate | 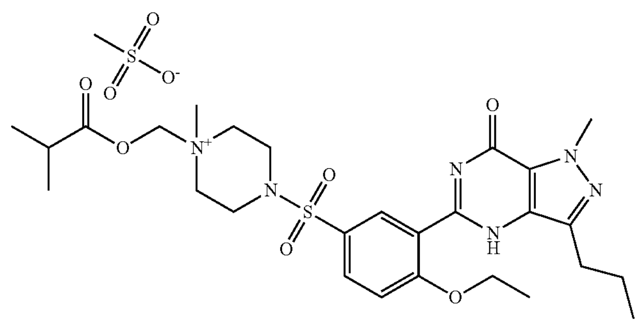 |
| 1038 | 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropoxycarbonyl)oxy)methyl)-1-methylpiperazin-1-ium iodide | 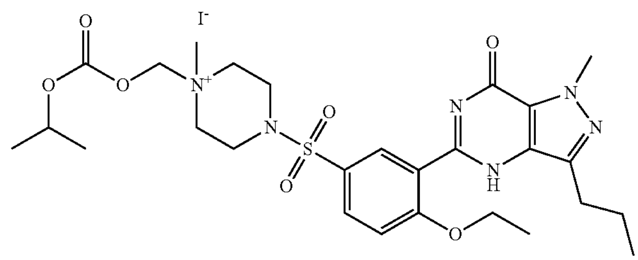 [SMILES: [I-] ; CCCc1nn(C)c2c(=O)nc(-c3cc(S(=O)(=O)N4CC[N+](C)(COC(=O)OC(C)C)CC4)ccc3OCC)[nH]c12] |
| 1039 | 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropoxycarbonyl)oxy)methyl)-1-methylpiperazin-1-ium methanesulfonate | 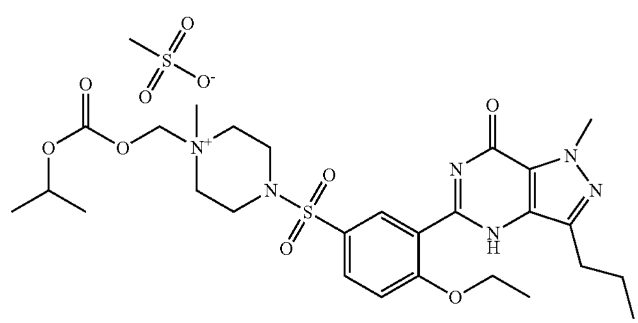 |
| 1040 | 1-(acetoxymethyl)-4-((4-ethoxy-3-(1-methyl-7-oxo-3-propyl-4,7-dihydro-1H-pyrazolo[4,3-d]pyrimidin-5-yl)phenyl)sulfonyl)-1-methylpiperazin-1-ium iodide | 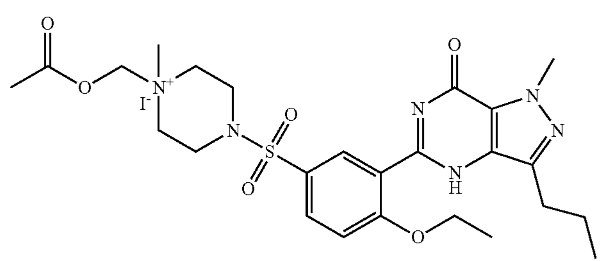 [SMILES: CCCc1nn(C)c2c(=O)nc(-c3cc(S(=O)(=O)N4CC[N+](C)(COC(C)=O)CC4)ccc3OCC)[nH]c12 ; [I-]] |
| 1041 | 1-(acetoxymethyl)-4-((4-ethoxy-3-(1-methyl-7-oxo-3-propyl-4,7-dihydro-1H-pyrazolo[4,3-d]pyrimidin-5-yl)pheny)sulfonyl)-1-methylpiperazin-1-ium methanesulfonate | 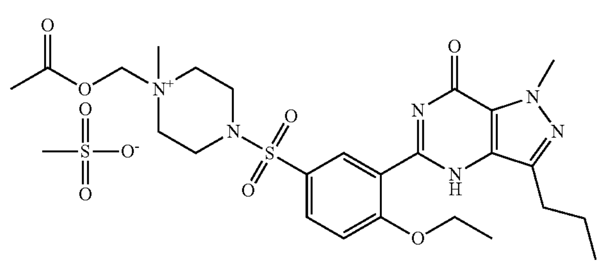 |

TABLE 1-continued

Illustrative compounds of the present invention

| No. | IUPAC name | Structure |
|---|---|---|
| 1042 | 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropylcarbamoyl)oxy)methyl)-1-methylpiperazin-1-ium methanesulfonate | 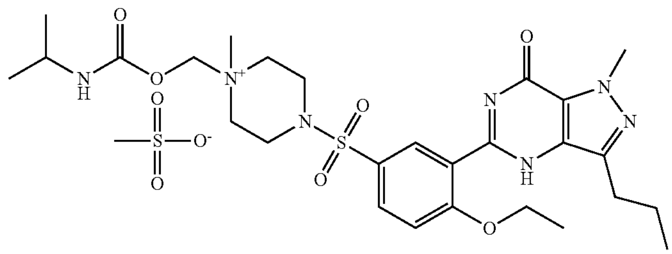 |
| 1043 | 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropylcarbamoyl)oxy)methyl)-1-methylpiperazin-1-ium iodide | 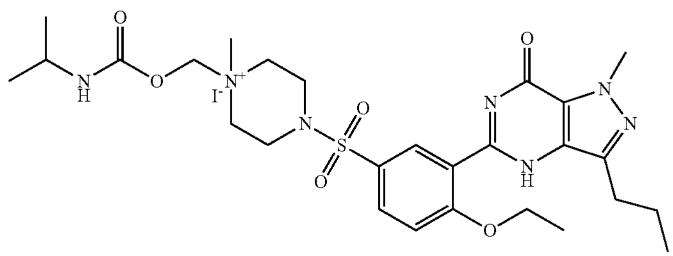 [SMILES: CCCc1nn(C)c2c(=O)nc(-c3cc(S(=O)(=O)N4CC[N+](C)(COC(=O)NC(C)C)CC4)ccc3OCC)[nH]c12 ; [I-]] |
| 1044 | (S)-1-((((2-(carboxymethyl)-4-methylpentyl)carbamoyl)oxy)methyl)-3-(methylcarbamoyl)pyridin-1-ium methanesulfonate | 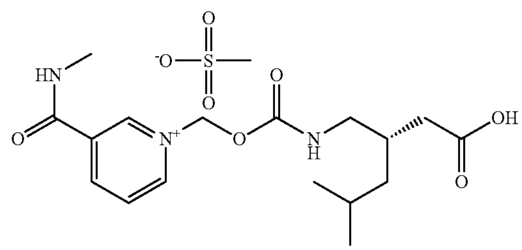 |
| 1045 | (S)-3-carbamoyl-1-((((2-(carboxymethyl)-4-methylpentyl)carbamoyl)oxy)methyl)pyridin-1-ium methanesulfonate | 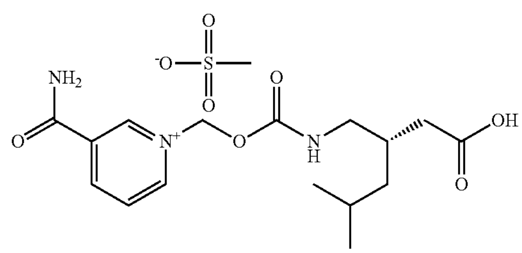 |
| 1046 | (S)-1-(((3-(aminomethyl)-5-methylhexanoyl)oxy)methyl)-3-(dimethylcarbamoyl)pyridin-1-ium methanesulfonate | 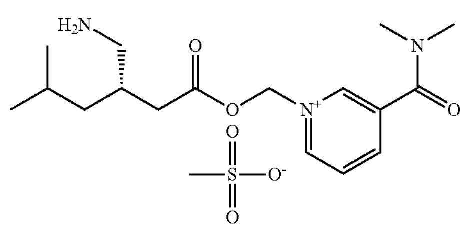 |
| 1047 | (S)-1-(((3-(aminomethyl)-5-methylhexanoyl)oxy)methyl)-3-(methylcarbamoyl)pyridin-1-ium methanesulfonate | 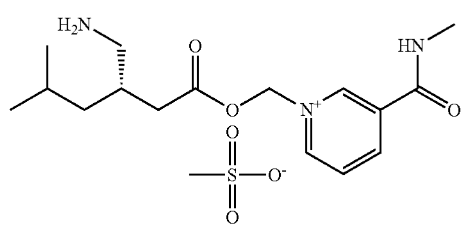 |

TABLE 1-continued

Illustrative compounds of the present invention

| No. | IUPAC name | Structure |
|---|---|---|
| 1048 | (S)-1-(((3-(aminomethyl)-5-methylhexanoyl)oxy)methyl)-3-carbamoylpyridin-1-ium methanesulfonate | 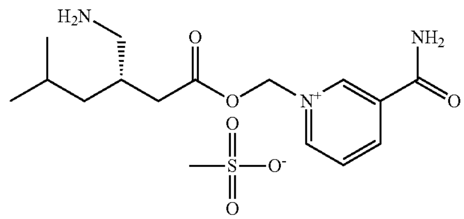 |
| 1049 | 3-(dimethylcarbamoyl)-1-((((4-((1E,4Z,6E)-5-hydroxy-7-(4-hydroxy-3-methoxyphenyl)-3-oxohepta-1,4,6-trien-1-yl)-2-methoxyphenoxy)carbonyl)oxy)methyl)pyridin-1-ium methanesulfonate | 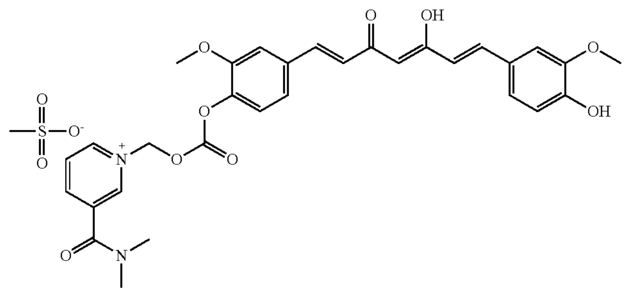 |
| 1050 | 1-((((4-((1E,4Z,6E)-5-hydroxy-7-(4-hydroxy-3-methoxyphenyl)-3-oxohepta-1,4,6-trien-1-yl)-2-methoxyphenoxy)carbonyl)oxy)methyl)-3-(methylcarbamoyl)pyridin-1-ium methanesulfonate | 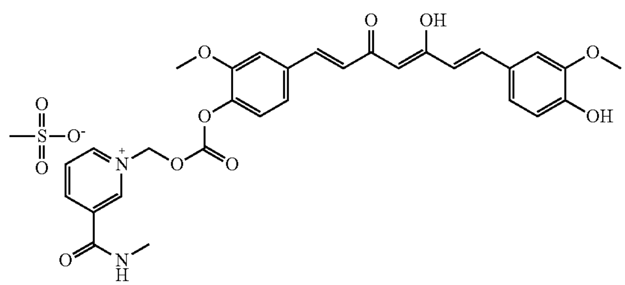 |
| 1051 | 3-carbamoyl-1-((((4-((1E,4Z,6E)-5-hydroxy-7-(4-hydroxy-3-methoxyphenyl)-3-oxohepta-1,4,6-trien-1-yl)-2-methoxyphenoxy)carbonyl)oxy)methyl)pyridin-1-ium methanesulfonate | 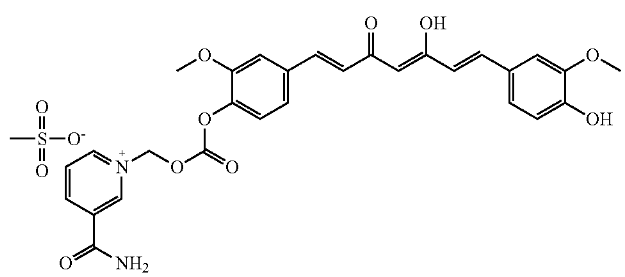 |
| 1052 | 3-(dimethylcarbamoyl)-1-((((1-phenylpropan-2-yl)carbamoyl)oxy)methyl)pyridin-1-ium methanesulfonate | 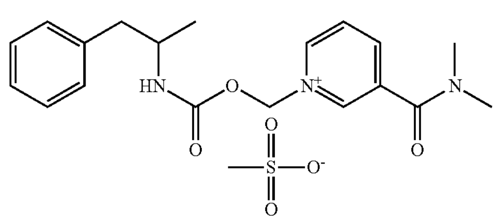 |

TABLE 1-continued

Illustrative compounds of the present invention

| No. | IUPAC name |
|---|---|
| 1053 | 1-((((1-carboxy-2-(3,4-dihydroxyphenyl)ethyl)carbamoyl)oxy)methyl)-3-(dimethylcarbamoyl)pyridin-1-ium methanesulfonate |
| 1054 | 1-((((1-carboxy-2-(3,4-dihydroxyphenyl)ethyl)carbamoyl)oxy)methyl)-3-(methylcarbamoyl)pyridin-1-ium methanesulfonate |
| 1055 | 3-carbamoyl-1-((((1-carboxy-2-(3,4-dihydroxyphenyl)ethyl)carbamoyl)oxy)methyl)pyridin-1-ium methanesulfonate |
| 1056 | 1-((((3,4-dihydroxyphenethyl)carbamoyl)oxy)methyl)-3-(dimethylcarbamoyl)pyridin-1-ium methanesulfonate |

TABLE 1-continued

Illustrative compounds of the present invention

| No. | IUPAC name |
|---|---|
| 1057 | 1-((((3,4-dihydroxyphenethyl)carbamoyl)oxy)methyl)-3-(methylcarbamoyl)pyridin-1-ium methanesulfonate |
| 1058 | 3-carbamoyl-1-((((3,4-dihydroxyphenethyl)carbamoyl)oxy)methyl)pyridin-1-ium methanesulfonate |
| 1059 | 1-((((4-acetamidophenoxy)carbonyl)oxy)methyl)-3-(dimethylcarbamoyl)pyridin-1-ium mesylate |
| 1060 | 1-((((2,6-diisopropylphenoxy)carbonyl)oxy)methyl)-3-(methoxycarbonyl)pyridin-1-ium iodide |
| 1061 | 3-carboxy-1-((((2,6-diisopropylphenoxy)carbonyl)oxy)methyl)pyridin-1-ium iodide |
| 1062 | 2-(((2,6-diisopropylphenoxy)carbonyl)oxy)-N,N,N-trimethylethan-1-aminium iodide |

TABLE 1-continued

Illustrative compounds of the present invention

| No. | IUPAC name | Structure |
|---|---|---|
| 1063 | 2-(((2,6-diisopropylphenoxy)carbonyl)oxy)-N,N-dimethylethan-1-aminium chloride | 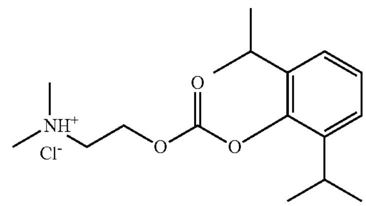 [SMILES: CC(C)c1cccc(C(C)C)c1OC(=O)OCC[NH+](C)C ; [Cl-]] |
| 1064 | 1-((((2,6-diisopropylphenoxy)carbonyl)oxy)methyl)-3-(hydroxycarbamoyl)pyridin-1-ium iodide | 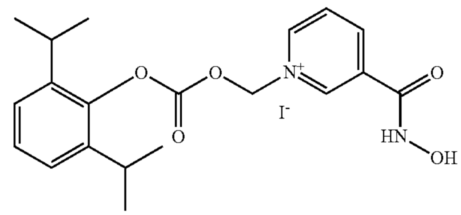 [SMILES: CC(C)c1cccc(C(C)C)c1OC(=O)OC[n+]1cccc(C(=O)NO)c1 ; [I-]] |
| 1065 | 3-(((((2,6-diisopropylphenoxy)carbonyl)oxy)methyl)carbamoyl)-1-methylpyridin-1-ium iodide | 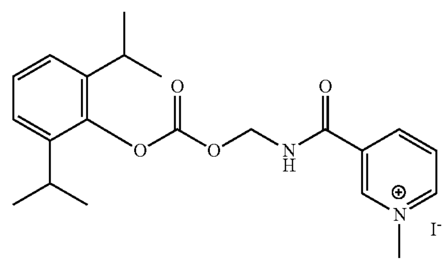 [SMILES: CC(C)c1cccc(C(C)C)c1OC(=O)OCNC(=O)c1ccc[n+](C)c1 ; [I-]] |
| 1066 | 1-(((2,6-diisopropylphenoxy)carbonyl)oxy)-N-((((2,6-diisopropylphenoxy)carbonyl)oxy)methyl)-N,N-dimethyl-methanaminium iodide | 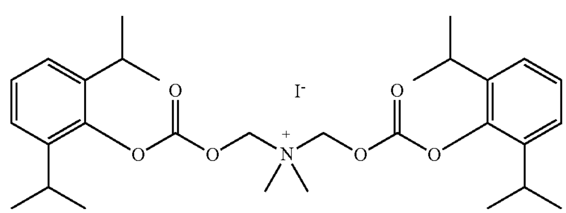 |
| 1067 | 2-(((2,6-diisopropylphenoxy)carbonyl)oxy)-N-((((2,6-diisopropylphenoxy)carbonyl)oxy)methyl)-N,N-dimethylethan-1-aminium iodide | 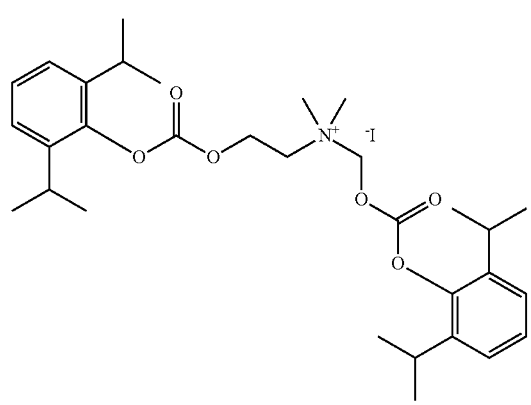 |

TABLE 1-continued

Illustrative compounds of the present invention

| No. | IUPAC name | Structure |
|---|---|---|
| 1068 | 1-((((2,6-diisopropylphenoxy)carbonyl)oxy)methyl)-4-formyl-3-hydroxy-5-(hydroxymethyl)-2-methylpyridin-1-ium iodide | 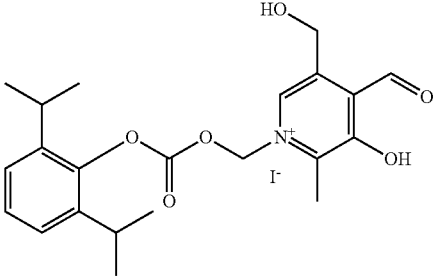 [SMILES: Cc1c(O)c(C=O)c(CO)c[n+]1COC(=O)Oc1c(C(C)C)cccc1C(C)C ; [I-]] |
| 1069 | 3-((2,6-diisopropylphenoxy)carbonyl)-1-((((2,6-diisopropylphenoxy)carbonyl)oxy)methyl)pyridin-1-ium methanesulfonate | 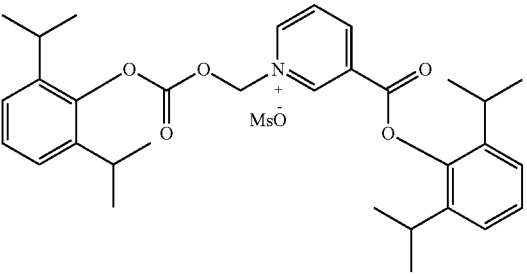 |
| 1070 | 2-(((2,6-diisopropylphenoxy)carbonyl)oxy)-N,N,N-trimethylethan-1-aminium methanesulfonate | 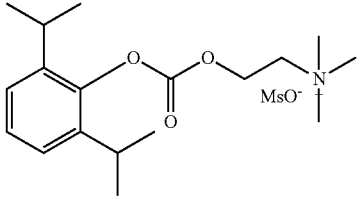 |
| 1071 | 1-(((11-cyclopropyl-4-methyl-6-oxo-6,11-dihydro-5H-dipyrido[3,2-b:2',3'-e][1,4]diazepine-5-carbonyl)oxy)methyl)-3-(methylcarbamoyl)pyridin-1-ium methanesulfonate | 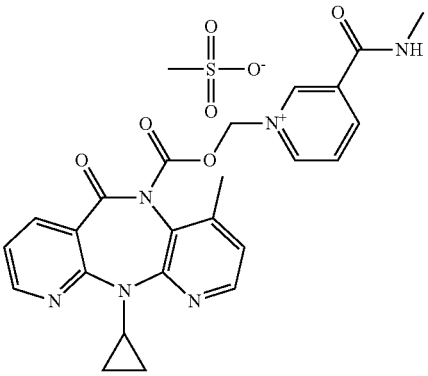 |
| 1072 | 1-(((11-cyclopropyl-4-methyl-6-oxo-6,11-dihydro-5H-dipyrido[3,2-b:2',3'-e][1,4]diazepine-5-carbonyl)oxy)methyl)-3-(dimethylcarbamoyl)pyridin-1-ium methanesulfonate | 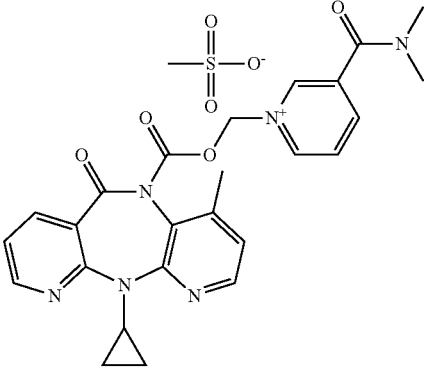 |

TABLE 1-continued

Illustrative compounds of the present invention

| No. | IUPAC name | Structure |
|-----|------------|-----------|
| 1073 | 3-carbamoyl-1-(((11-cyclopropyl-4-methyl-6-oxo-6,11-dihydro-5H-dipyrido[3,2-b:2',3'-e][1.4]diazepine-5-carbonyl)oxy)methyl)pyridin-1-ium methanesulfonate | 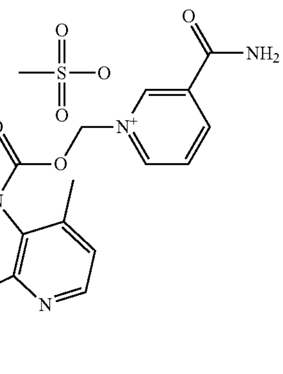 |
| 1074 | 3-(dimethylcarbamoyl)-1-((2-(4-isobutylphenyl)propanoyloxy)methyl) pyridinium mesylate | 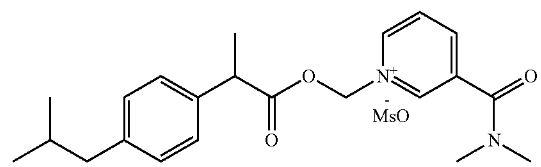 [SMILES: CC(C)Cc1ccc(C(C)C(=O)OC[n+]2cccc(C(=O)N(C)C)c2)cc1] |
| 1075 | (S)-1-((((2-(carboxymethyl)-2,4-dimethylpentyl)carbamoyl)oxy)methyl)-3-(dimethylcarbamoyl)pyridin-1-ium iodide | 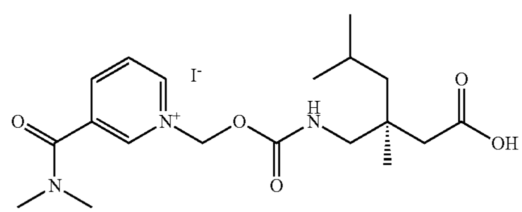 [SMILES: CC(C)C[C@](C)(CNC(=O)OC[n+]1cccc(C(=O)N(C)C)c1)CC(=O)O ; [I-]] |
| 1076 | (S)-1-((((2-(carboxymethyl)-2,4-dimethylpentyl)carbamoyl)oxy)methyl)-3-(dimethylcarbamoyl)pyridin-1-ium methanesulfonate | 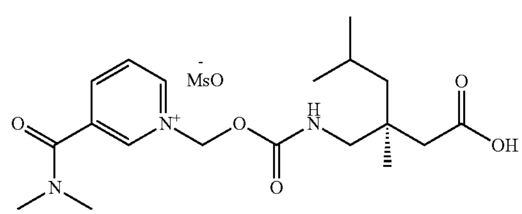 [SMILES: CC(C)C[C@](C)(CNC(=O)OC[n+]1cccc(C(=O)N(C)C)c1)CC(=O)O] |
| 1077 | 3-carbamoyl-1-(((((2,6-diisopropylphenoxy)carbonyl)oxy)methyl) pyridin-1-ium bromide | 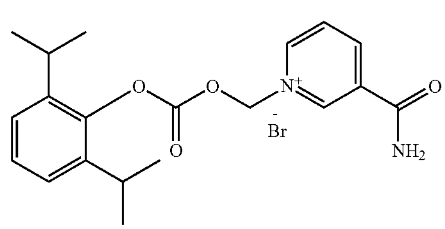 [SMILES: CC(C)c1cccc(C(C)C)c1OC(=O)OC[n+]1cccc(C(N)=O)c1 ; Br] |
| 1078 | 3-carbamoyl-1-(((((2,6-diisopropylphenoxy)carbonyl)oxy)methyl) pyridin-1-ium chloride | 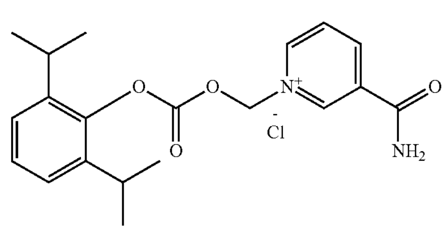 [SMILES: CC(C)c1cccc(C(C)C)c1OC(=O)OC[n+]1cccc(C(N)=O)c1 ; Cl] |

TABLE 1-continued

Illustrative compounds of the present invention

| No. | IUPAC name |
|---|---|
| 1079 | 1-((((2,6-diisopropylphenoxy)carbonyl)oxy)methyl)-3-(methylcarbamoyl)pyridin-1-ium tetrafluoroborate |
| 1080 | 1-((((2,6-diisopropylphenoxy)carbonyl)oxy)methyl)-3-(methylcarbamoyl)pyridin-1-ium nitrate |
| 1081 | 1-((((2,6-diisopropylphenoxy)carbonyl)oxy)methyl)-3-(methylcarbamoyl)pyridin-1-ium chloride |
| 1082 | 1-((((2,6-diisopropylphenoxy)carbonyl)oxy)methyl)-3-(methoxycarbonyl)pyridin-1-ium methanesulfonate |
| 1083 | 3-carboxy-1-((((2,6-diisopropylphenoxy)carbonyl)oxy)methyl)pyridin-1-ium methanesulfonate |

The compounds of the present invention include:

i. 1-(((2,6-diisopropylphenoxy)carbonyloxy)methyl)-3-(dimethylcarbamoyl)pyridinium mesylate;

ii. 1-(((2,6-diisopropylphenoxy)carbonyloxy)methyl)-3-(methylcarbamoyl)pyridinium mesylate;

iii. 3-carbamoyl-1-(((2,6-diisopropylphenoxy)carbonyloxy)methyl)pyridinium mesylate; 1-(((2,6-diisopropylphenoxy)carbonyloxy)methyl)-3-(methylcarbamoyl)pyridinium iodide;

iv. (E)-3-(dimethylcarbamoyl)-1-(((2-methoxy-4-((8-methylnon-6-enamido)methyl) phenoxy)carbonyloxy)methyl)pyridinium iodide;

v. (E)-3-(dimethylcarbamoyl)-1-(((2-methoxy-4-((S-methylnon-6-enamido)methyl)phenoxy)carbonyloxy)methyl)pyridinium mesylate;

vi. 3-(dimethylamino)-1-(((4-((1E,4Z,6E)-5-hydroxy-7-(4-hydroxy-3-methoxyphenyl)-3-oxohepta-1,4,6-trienyl)-2-methoxyphenoxy)carbonyloxy)methyl)pyridinium iodide;

vii. 3-(dimethylcarbamoyl)-1-((2-(4-isobutylphenyl)propanoyloxy)methyl)pyridinium iodide;

viii. 1-((2-acetoxybenzoyloxy)methyl)-3-carbamoylpyridinium iodide;

ix. 1-((2-acetoxybenzoyloxy)methyl)-3-(methylcarbamoyl)pyridinium iodide;

x. 1-((2-acetoxybenzoyloxy)methyl)-3-(dimethylcarbamoyl)pyridinium iodide;

xi. 1-((2-acetoxybenzoyloxy)methyl)-3-carbamoylpyridiniummesylate;

xii. 1-((2-acetoxybenzoyloxy)methyl)-3-(dimethylkcarbamoyl)pyridiniummesylate;

xiii. 1-((2-acetoxybenzoyloxy)methyl)-3-(methylcarbamoyl)pyridinium mesylate;
xiv. 3-carbamoyl-1-((2-(1-(4-chlorobenzoyl)-5-methoxy-2-methyl-1H-indol-3-yl)acetoxy)methyl)pyridinium iodide;
xv. 1-((2-(1-(4-chlorobenzoyl)-5-methoxy-2-methyl-1H-indol-3-yl)acetoxy)methyl)-3-(dimethylcarbamoyl)pyridinium iodide;
xvi. 1-((2-(1-(4-chlorobenzoyl)-5-methoxy-2-methyl-1H-indol-3-yl)acetoxy)methyl)-3-(dimethylcarbamoyl)pyridinium mesylate;
xvii. 1-((2-(2-(2,6-dichlorophenylamino)phenyl)acetoxy)methy)-3-dimethylcarbamoyl)pyridinium iodide;
xviii. 1-(2-(4-acetamidophenoxy)-2-oxoethyl)-3-dimethylcarbamoyl)pyridin-1-ium iodide;
xix. 1-((((((1S,2R)-1-benzamido-3-(((2aR,4S,4aS,6R,9S,11S,12S,12aR,12bS)-6,12b-diacetoxy-12-(benzoyloxy)-4-((((3-(dimethylcarbamoyl)pyridin-1-ium-1-yl)methoxy)carbonyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium diiodide;
xx. 1-(((6R,7R)-7-((E)-2-(2-aminothiazol-4-yl)-2-(methoxyimino)acetamido)-3-(methoxymethyl)-5-oxo-5-thia-1-azabicyclo[4.2.0]oct-2-ene-2-carbonyl)oxy)methyl)-3-(dimethylcarbamoyl)pyridin-1-ium methane sulfonate;
xxi. L(S)-1-((2-(carboxymethyl)-4-methylpentylcarbamoyloxy)methyl)-3-(dimethylcarbamoyl)pyridinium methanesulfonate;
xxii. (S)-1-((2-(carboxymethyl)-4-methylpentylcarbamoyloxy)methyl)-3-(dimethylcarbamoyl)pyridinium iodide;
xxiii. 1-((2-((E)-1-(2-aminothiazol-4-yl)-2-((1S,8R)-5-(((3-(dimethylcarbamoyl)pyridinium-1-yl)methoxy)carbonyl)-7-oxo-4-vinyl-2-thiabicyclo[4.2.0]oct-4-en-8-ylamino)-2-oxoethylideneamninooxy)acetoxy)methyl)-3-(dimethylcarbamoyl)pyridinium;
xxiv. 1-((2-((E)-1-(2-aminothiazol-4-yl)-2-((1S,8R)-5-(((3-(dimethylcarbamoyl)pyridinium-1-yl)methoxy)carbonyl)-7-oxo-4-vinyl-2-thiabicyclo[4.2.0]oct-4-en-8-ylamino)-2-oxoethylideneaminooxy)acetoxy)methyl)-3-(dimethylcarbamoyl)pyridinium;
xxv. 1-((4-((E)-2-((6R,7R)-2-carboxy-8-oxo-3-vinyl-5-thia-1-azabicyclo[4.2.0]oct-2-en-7-ylamino)-1-(carboxymethoxy)-2-oxoethyl)thiazol-2-ylcarbamoyloxy)methyl)-3-(dimethylcarbamoyl)pyridinium;
xxvi. 1-((((2,6-diisopropylphenoxy)carbonyl)oxy)methyl)-3-(dimethylcarbamoyl)pyridin-1-ium methanesulfonate;
xxvii. 1-((((2,6-diisopropylphenoxy)carbonyl)oxy)methyl)-3-(dimethylcarbamoyl)pyridin-1-ium iodide;
xxviii. 3-carbamoyl-1-((((2,6-diisopropyl-phenoxy)carbonyl)oxy)methyl)pyridin-1-ium iodide;
xxix. 1-(((isopropylcarbamoyl)oxy)methyl)-3-(2-((2-methyl-5-((3-(4-methyl-1H-imidazol-3-ium-1-yl)-5-(trifluoromethyl)phenyl)carbamoyl)phenyl)amino)pyrimidin-4-yl)pyridin-1-ium methanesulfonate;
xxx. 1-(((isopropoxycarbonyl)oxy)methyl)-3-(2-((2-methyl-5-((3-(4-methyl-1H-imidazol-3-ium-1-yl)-5-(trifluoromethyl)phenyl)carbamoyl)phenyl)amino)pyrimidin-4-yl)pyridin-1-ium methanesulfonate;
xxxi. 3-(2-((2-methyl-5-((3-(4-methyl-1H-imidazol-3-ium-1-yl)-5-(trifluoromethyl)phenyl)carbamoyl)phenyl)amino)pyrimidin-4-yl)-1-((2-phenylacetoxy)methyl)pyridin-1-ium methanesulfonate;
xxxii. 1-((isobutyryloxy)methyl)-3-(2-((2-methyl-5-((3-(4-methyl-1H-imidazol-3-ium-1-yl)-5-(trifluoromethyl)phenyl)carbamoyl)phenyl)amino)pyrimidin-4-yl)pyridin-1-ium methanesulfonate;
xxxiii. 4-((4-ethoxy-3-(1-methyl-7-oxo-3-propyl-4,7-dihydro-1H-pyrazolo[4,3-d]pyrimidin-5-yl)phenyl)sulfonyl)-1-((isobutyryloxy)methyl)-1-methylpiperazin-1-ium iodide;
xxxiv. 4-((4-ethoxy-3-(1-methyl-7-oxo-3-propyl-4,7-dihydro-1H-pyrazolo[4,3-d]pyrimidin-5-yl)phenyl)sulfonyl)-1-((isobutyryloxy)methyl)-1-methylpiperazin-1-ium methanesulfonate;
xxxv. 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropoxycarbonyl)oxy)methyl)-1-methylpiperazin-1-ium iodide;
xxxvi. 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropoxycarbonyl)oxy)methyl)-1-methylpiperazin-1-ium methanesulfonate;
xxxvii. 1-(acetoxymethyl)-4-((4-ethoxy-3-(1-methyl-7-oxo-3-propyl-4,7-dihydro-1H-pyrazolo[4,3-d]pyrimidin-5-yl)phenyl)sulfonyl)-1-methylpiperazin-1-ium iodide;
xxxviii. 1-(acetoxymethyl)-4-((4-ethoxy-3-(1-methyl-7-oxo-3-propyl-4,7-dihydro-1H-pyrazolo[4,3-d]pyrimidin-5-yl)phenyl)sulfonyl)-1-methylpiperazin-1-ium methanesulfonate;
xxxix. 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropylcarbamoyl)oxy)methyl)-1-methylpiperazin-1-ium methanesulfonate;
xl. 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropylcarbamoyl)oxy)methyl)-1-methylpiperazin-1-ium iodide;
xli. (S)-1-((((2-(carboxymethyl)-4-methylpentyl)carbamoyl)oxy)methyl)-3-(methylcarbamoyl)pyrindin-1-ium methanesulfonate;
xlii. (S)-3-carbamoyl-1-((((2-(carboxymethyl)-4-methylpentyl)carbamoyl)oxy)methyl)pyridin-1-ium methanesulfonate;
xliii. (S)-1-(((3-(aminomethyl)-5-methylhexanoyl)oxy)methyl)-3-(dimethylcarbamoyl)pyridin-1-ium methanesulfonate;
xliv. (S)-1-(((3-(aminomethyl)-5-methylhexanoyl)oxy)methyl)-3-(methylcarbamoyl)pyridin-1-ium methanesulfonate;
xlv. (S)-1-(((3-(aminomethyl)-5-methylhexanoyl)oxy)methyl)-3-carbamoylpyridin-1-ium methanesulfonate;
xlvi. 3-(dimethylcarbamoyl)-1-((((4-((1E,4Z,6E)-5-hydroxy-7-(4-hydroxy-3-methoxy-phenyl)-3-oxohepta-1,4,6-trien-1-yl)-2-methoxyphenoxy)carbonyl)oxy)methyl)pyridin-1-ium methanesulfonate;
xlvii. 1-(((((4-((1E,4Z,6E)-5-hydroxy-7-(4-hydroxy-3-methoxyphenyl)-3-oxohepta-1,4,6-trien-1-yl)-2-methoxyphenoxy)carbonyl)oxy)methyl)-3-(methyl-carbamoyl)pyridin-1-ium methanesulfonate;
xlviii. 3-carbamoyl-1-((((4-((1E,4Z,6E)-5-hydroxy-7-(4-hydroxy-3-methoxyphenyl)-3-oxohepta-1,4,6-trien-1-yl)-2-methoxy-phenoxy)carbonyl)oxy)methyl)pyridin-1-ium methanesulfonate;
xlix. 3-(dimethylcarbamoyl)-1-(((((1-phenylpropan-2-yl)carbamoyl)oxy)methyl)pyridin-1-ium methanesulfonate;
l. 1-((((1-carboxy-2-(3,4-dihydroxyphenyl)ethyl)carbamoyl)oxy)methyl)-3-(dimethylcarbamoyl)pyridin-1-ium methanesulfonate;

li. 1-((((1-carboxy-2-(3,4-dihydroxyphenyl)ethyl)carbamoyl)oxy)methyl)-3-(methylcarbamoyl)pyridin-1-ium methanesulfonate;

lii. 3-carbamoyl-1-((((1-carboxy-2-(3,4-dihydroxyphenyl)ethyl)carbamoyl)oxy)methyl)pyridin-1-ium methanesulfonate;

liii. 1-((((3,4-dihydroxyphenethyl)carbamoyl)oxy)methyl)-3-(dimethylcarbamoyl)pyridin-1-ium methanesulfonate;

liv. 1-((((3,4-dihydroxyphenethyl)carbamoyl)oxy)methyl)-3-(methylcarbamoyl)pyridin-1-ium methanesulfonate;

lv. 3-carbamoyl-1-((((3,4-dihydroxy-phenethyl)carbamoyl)oxy)methyl)pyridin-1-ium methanesulfonate;

lvi. 1-((((4-acetamidophenoxy)carbonyl)oxy)methyl)-3-(dimethylcarbamoyl)pyridin-1-ium mesylate;

lvii. 1-((((2,6-diisopropylphenoxy)carbonyl)oxy)methyl)-3-(methoxycarbonyl)pyridin-1-ium iodide;

lviii. 3-carboxy-1-((((2,6-diisopropylphenoxy)carbonyl)oxy)methyl)pyridin-1-ium iodide;

lix. 2-(((2,6-diisopropylphenoxy)carbonyl)oxy)-N,N,N-trimethylethan-1-aminium iodide;

lx. 2-(((2,6-diisopropylphenoxy)carbonyl)oxy)-N,N-dimethylethan-1-aminium chloride;

lxi. 1-((((2,6-diisopropylphenoxy)carbonyl)oxy)methyl)-3-(hydroxycarbamoyl)pyridin-1-ium iodide;

lxii. 3-(((((2,6-diisopropylphenoxy)carbonyl)oxy)methyl)carbamoyl)-1-methylpyridin-1-ium iodide;

lxiii. 1-(((2,6-diisopropylphenoxy)carbonyl)oxy)-N-((((2,6-diisopropylphenoxy)carbonyl)oxy)methyl)-N,N-dimethylmethanaminium iodide;

lxiv. 2-(((2,6-diisopropylphenoxy)carbonyl)oxy)-N-((((2,6-diisopropylphenoxy)carbonyl)oxy)methyl)-N,N-dimethylethan-1-aminium iodide;

lxv. 1-((((2,6-diisopropylphenoxy)carbonyl)oxy)methyl)-4-formyl-3-hydroxy-5-(hydroxymethyl)-2-methylpyridin-1-ium iodide;

lxvi. 3-((2,6-diisopropylphenoxy)carbonyl)-1-((((2,6-diisopropylphenoxy)carbonyl)oxy)methyl)pyridin-1-ium methanesulfonate;

lxvii. 2-(((2,6-diisopropylphenoxy)carbonyl)oxy)-N,N,N-trimethylethan-1-aminium methanesulfonate;

lxviii. 1-(((11-cyclopropyl-4-methyl-6-oxo-6,11-dihydro-5H-dipyrido[3,2-b:2',3'-e][1,4]diazepine-5-carbonyl)oxy)methyl)-3-(methylcarbamoyl)pyridin-1-ium methanesulfonate;

lxix. 1-(((11-cyclopropyl-4-methyl-6-oxo-6,11-dihydro-5H-dipyrido[3,2-b:2',3'-e][1,4]diazepine-5-carbonyl)oxy)methyl)-3-(dimethylcarbamoyl)pyridin-1-ium methanesulfonate;

lxx. 3-carbamoyl-1-(((11-cyclopropyl-4-methyl-6-oxo-6,11-dihydro-5H-dipyrido[3,2-b:2',3'-e][1,4]diazepine-5-carbonyl)oxy)methyl)pyridin-1-ium methanesulfonate.

lxxi. 3-(dimethylcarbamoyl)-1-((2-(4-isobutylphenyl)propanoyloxy)methyl)pyridinium mesylate;

lxxii. (S)-1-(((((2-(carboxymethyl)-2,4-dimethylpentyl)carbamoyl)oxy)methyl)-3-(dimethylcarbamoyl)pyridin-1-ium methanesulfonate;

lxxiii. 3-carbamoyl-1-(((11-cyclopropyl-4-methyl-6-oxo-6,11-dihydro-5H-dipyrido[3,2-b:2',3'-e][1,4]diazepine-5-carbonyl)oxy)methyl)pyridin-1-ium methanesulfonate;

lxxiv. 3-carbamoyl-1-((((2,6-diisopropylphenoxy)carbonyl)oxy)methy)pyridin-1-ium bromide;

lxxv. 3-carbamoyl-1-((((2,6-diisopropylphenoxy)carbonyl)oxy)methyl)pyridin-1-ium chloride;

lxxvi. 1-((((2,6-diisopropylphenoxy)carbonyl)oxy)methyl)-3-(methylcarbamoyl)pyridin-1-ium tetrafluoroborate;

lxxvii. 1-((((2,6-diisopropylphenoxy)carbonyl)oxy)methyl)-3-(methylcarbamoyl)pyridin-1-ium nitrate;

lxxviii. 1-((((2,6-diisopropylphenoxy)carbonyl)oxy)methyl)-3-(methylcarbamoyl)pyridin-1-ium chloride;

lxxix. 1-((((2,6-diisopropylphenoxy)carbonyl)oxy)methyl)-3-(methoxycarbonyl)pyridin-1-ium methanesulfonate;

lxxx. 3-carboxy-1-((((2,6-diisopropylphenoxy)carbonyl)oxy)methyl)pyridin-1-ium methanesulfonate.

D. Salts and Isomers and Counter Ions

The present invention includes within its scope the salts and isomers. Compounds of the present invention after being novel by the substituted methyl formyl reagent may in some cases form salts which are also within the scope of this invention. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety, such as a carboxyl group). Also included herein are quaternary ammonium salts such as alkyl ammonium salts.

Pharmaceutically acceptable (i.e., non-toxic, physiologically acceptable) salts are preferred, although other salts are useful, for example, in isolation or purification steps which may be employed during preparation. Salts of the compounds of may be formed, for example, by reacting a compound with an amount of acid or base, such as an equivalent amount, in a medium such as one in which the salt precipitates or in an aqueous medium followed by lypholization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxy ethanesulfonates, lactates, maleates, methanesulfonates. 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, wherein the substituent comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternmized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Solvates of the compounds of the invention are also contemplated herein. Solvates of the compounds of formula 1 are preferably hydrates or any other pharmaceutically acceptable solvate.

All stereoisomers of the present compounds, such as those which may exist due to asymmetric carbons on the R substituents of the compound, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention may have the S or R configuration.

The present invention also envisages within its scope the effect of selection of suitable counter ions. The counter ion of the compounds of the present invention may be chosen by selecting the dissociation constant for the drug capable of ionization within the said pH range. By estimating the ionized and un-ionized drug concentration of any compound (using well established equations such a Henderson-Hasselbach equation), the solubility and consequently the absorption of the drug may be novel.

The present invention includes in its scope, the modification of deuterated compounds. Deuterated compounds are those wherein the compounds have selective incorporation of deuterium in place of hydrogen. Deuterated compounds may be further novel by the substituted compounds of the present invention as per procedures as disclosed herein.

E. Composition Containing the Novel Entities of the Invention

The invention thus also provides the use of the novel entity as defined herein for use in human or veterinary medicine. The compound for use as a pharmaceutical may be presented as a pharmaceutical formulation.

The invention therefore provides in a further aspect a pharmaceutical formulation comprising the novel compounds of the invention with a pharmaceutically acceptable carrier thereof and optionally other therapeutic and/or prophylactic ingredients. The carriers must be "acceptable" in the sense of being compatible with the other ingredients of the formula and not deleterious to the recipient thereof. Suitably the pharmaceutical formulation will be in an appropriate unit dosage form.

The pharmaceutical formulations may be any formulation and include those suitable for oral, intranasal, intraocular or parenteral (including intramuscular and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both, and then, if necessary, shaping the product into the desired formulation.

For these purposes the compounds of the present invention may be administered orally, topically, intranasally, intraocularly, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasteral injection or infusion techniques. In addition to the treatment of warm-blooded animals such as mice, rats, horses, dogs, cats, etc., the compounds of the invention are effective in the treatment of humans.

EXAMPLES

Example 1

1-((((4-acetamidophenoxy)carbonyl)oxy)methyl)-3-(dimethylcarbamoyl)pyridin-1-ium mesylate [1059]

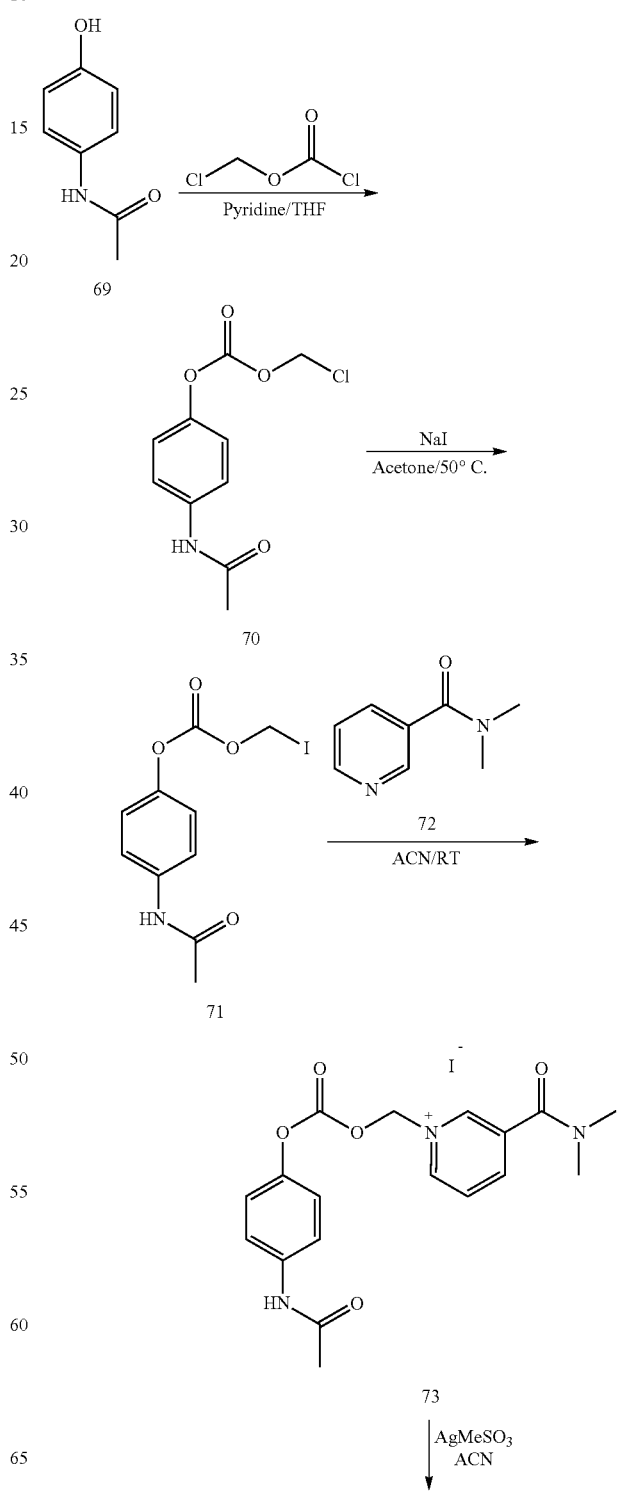

-continued

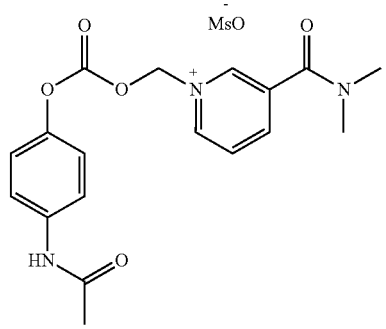

1059

Step 1:

Pyridine (0.375 g, 47.5 mmol. 2.5 eq) was added to a solution of chloromethyl chloroformate (CMCF) [69] (0.294 g, 22.8 mmol, 1.2 eq) in dry THF (10 ml) under an argon atmosphere at 00 C. At 0° C., a solution of N-(4-hydroxyphenyl)acetamide. N-(4-hydroxyphenyl)ethanamide [210] (0.300 g, 19.0 mmol. 1.0 eq) in dry THF was added to the above reaction mixture. The reaction mixture was stirred at room temperature for 20 h. reaction progress was monitored by TLC. After 20 h, the reaction mixture was diluted with dichloromethane (50 ml), washed with water (15 ml), 10% solution of NaHCO3 (15 ml), dil HCl (10 ml), followed by brine (10 ml), and the organic layer dried over anhydrous sodium sulfate. Evaporation of the solvents under vacuum gave the crude product. The crude product was purified by silica gel column chromatography (100-200 mesh) using MeOH: DCM (2%) as eluent to yield a off white product, 4-acetamidophenyl (chloromethyl) carbonate [76]. (0.330 g, 68%). m/z: 244

Step 2:

Sodium iodide (0.454 g, 107 mmol 3.7 eq) was added to a solution of 4-acetamidophenyl (chloromethyl) carbonate [76] (0.20 g, 29 mmol, 1.0 eq) in acetone. The resulting reaction mixture was heated for 6 h at 50° C. Reaction progress was monitored by TLC. The reaction mixture was cooled to room temperature and passed through a bed of silica (mesh 100-200). The silica bed was washed several times with acetone was and fractions collected and evaporated under vacuum to yield the desired product, 4-acetamidophenyl (iodomethyl) carbonate [38], (0.27 g, 98%). m/z: 336

Step 3:

Dimethyl nicotinamide [72] (0.022 g, 15 mmol, 1.0 eq) was added to a solution of 4-acetamidophenyl (iodomethyl) carbonate [71], (0.05 g, 15 mmol, 1.0 eq) in dry acetonitrile (2 ml) under argon atmosphere. The resulting reaction mixture was stirred for 2 days at RT. Reaction progress was monitored by TLC. Solvent was removed under vacuum to get a crude product. The crude product obtained was triturated with diethyl ether (10 ml×2) to give the desired product, 1-((((4-acetamidophenoxy)carbonyl)oxy)methyl)-3-(dimethylcarbamoyl)pyridin-1-ium iodide [73] (0.021 g, 29%). m/z: 358.

Step 4:

To a stirred solution of 1-((((4-acetamidophenoxy)carbonyl)oxy)methyl)-3-(dimethyl-carbamoyl)pyridin-1-ium [73] (0.0163 g, 0.027 mmol, 1.0 eq) in ACN (2 ml) was added silver(I) methanesulfonate (0.0054 g, 0.027 mmol, 1.0 eq) at RT. The reaction mixture was stirred at RT for 2 h. The reaction was filtered to get rid of silver iodide. Filtrate was concentrated under vacuum, which was triturated with dry ether (2×5 ml), ether removed by decantation and product dried under vacuum to get the desired product 1-((((4-acetamidophenoxy)carbonyl)oxy)methyl)-3-(dimethylcarbamoyl)pyridin-1-ium mesylate [1059] (0.0122 g, 66%) as pale yellow solid. m/z: 358.

Example 2

Synthesis of 1-(((((S,2R)-1-benzamido-3-(((2aR, 4S,4 aS,6R,9S,11S,12S,12aR,12bS)-6,12b-diacetoxy-12-(benzoyloxy)-4-((((3-(dimethylcarbamoyl)pyridin-1-ium-1-yl)methoxy)carbonyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium diiodide [1023]

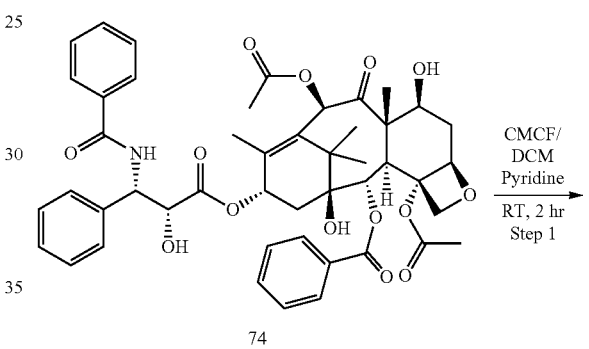

74

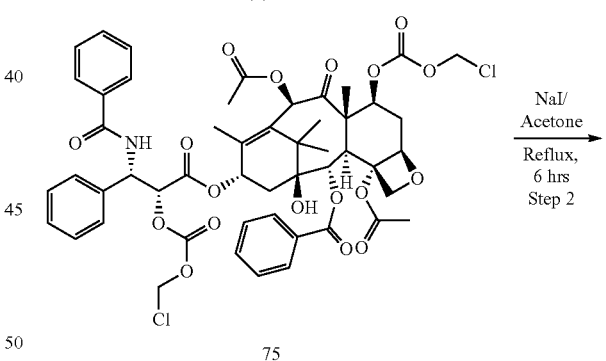

75

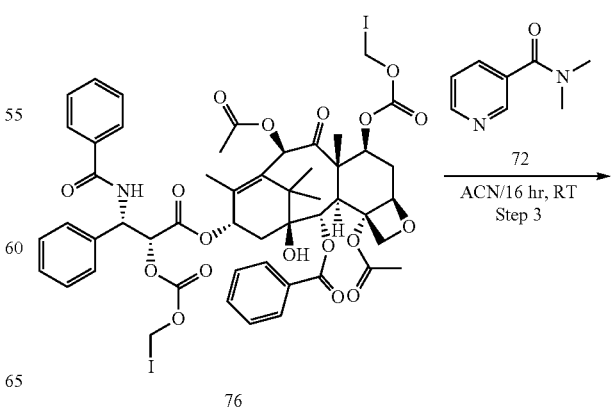

76

-continued

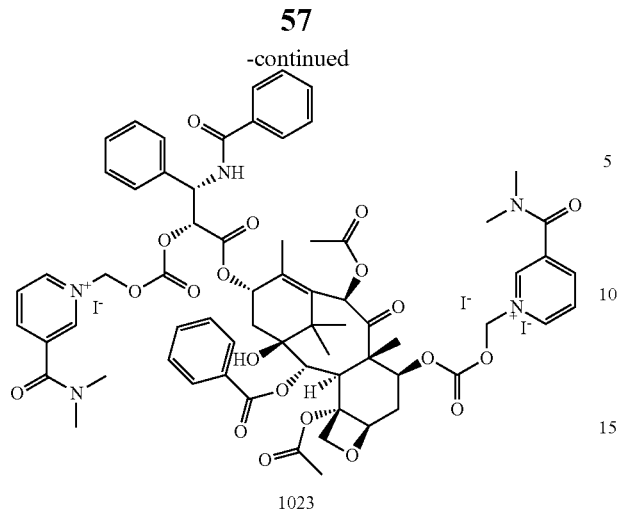

1023

Step 1:

Pyridine (0.026 g, 23.0 mmol, 2 eq) was added to a solution of chloromethyl chloroformate (CMCF) (0.020 g, 23.0 mmol, 2 eq) in dry dichloromethane under an argon atmosphere at 0° C. At 0° C., a solution of (2α,4α,5β,7β,10β)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate [74] (0.100 g, 11.7 mmol, 1 eq) in dry dichloromethane was added. The reaction mixture was stirred at room temperature for 2 hours. The reaction progress was monitored by TLC. After 2 hours the reaction mixture was diluted with dichloromethane (25 ml), washed with a 10% solution of NaHCO$_3$ (15 ml), brine (10 ml), and then dried over anhydrous sodium sulfate. Evaporation of the solvents gave the desired product, [75], (2aR, 4S,4aS,6R,9S,11S,12S,12aR,12bS)-9-(((2R,3S)-3-benzamido-2-(((chloromethoxy) carbonyl)oxy)-3-phenylpropanoyl)oxy)-12-(benzoyloxy)-4-(((chloromethoxy)carbonyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxete-6,12b-diyl diacetate, as a white solid (0.110 g, 90%). m/z=1038.3

Step 2:

Sodium iodide (22 mg, 145 mmol) was added to a solution of [75] (0.030 g, 29 mmol) in acetone. The resulting reaction mixture was refluxed for 6 hours at 60° C. Reaction progress was monitored by TLC. The reaction mixture was cooled to room temperature and passed through a bed of silica (mesh 100-200). The silica bed was washed with acetone which was collected and evaporated to yield the desired product [76], (2aR,4S,4aS,6R,9S,11S,12S,12aR, 12bS)-9-(((2R,3S)-3-benzamido-2-(((iodomethoxy) carbonyl)oxy)-3-phenylpropanoyl)oxy)-12-(benzoyloxy)-11-hydroxy-4-(((iodomethoxy) carbonyl)oxy)-4a,8,13,13-tetramethyl-5-oxo-2a,3,4,4a,5,6,9,10,1,12,12a,12b-dodecahydro-1H-7,11-methanocyclodeca[3,4]benzo[1,2-b]oxete-6,12b-diyl diacetate, as a white solid (0.020 g, 70%). m/z=1221.7

Step 3:

Dimethyl nicotinate [72] (0.003 g, 20 mmol) was added to a solution of [76] (0.010 g, 10 mmol) in dry acetonitrile under argon atmosphere. The resulting yellow reaction mixture was stirred for 16 hours at RT. Reaction progress was monitored by TLC. Solvent was removed under high vacuum pump to give a crude product. The crude product obtained was triturated with diethyl ether (10 ml×2) to give the desired product [1023], mono(1-((((((1S,2R)-1-benzamido-3-(((2aR,4S,4aS,6R,9S,11S,12S,12aR,12bS)-6,12b-diacetoxy-12-(benzoyloxy)-4-((((3-(dimethylcarbamoyl) pyridin-1-ium-1-yl)methoxy)carbonyl)oxy)-11-hydroxy-4a, 8,13,13-tetramethyl-5-oxo-2a,3,4,4a,5,6,9,10,11,12,12a, 12b-dodecahydro-1H-7,11-methanocyclodeca[3,4]benzo[1, 2-b]oxet-9-yl)oxy)-3-oxo-1-phenylpropan-2-yl)oxy) carbonyl)oxy)methyl)-3-(dimethylcarbamoyl)pyridin-1-ium) doiodide as a yellow solid (0.014 g, 60%). m/z=1268.

Example 3

Synthesis of 1-(2-(4-acetamidophenoxy)-2-oxo-ethyl)-3-(dimethylcarbamoyl)pyridin-1-ium iodide, [1022]

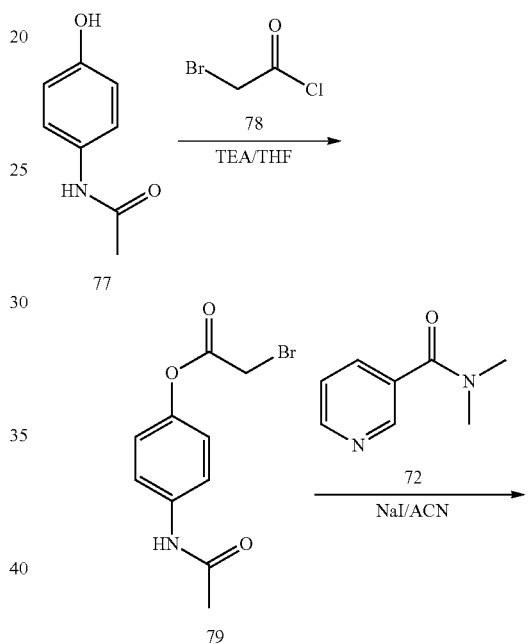

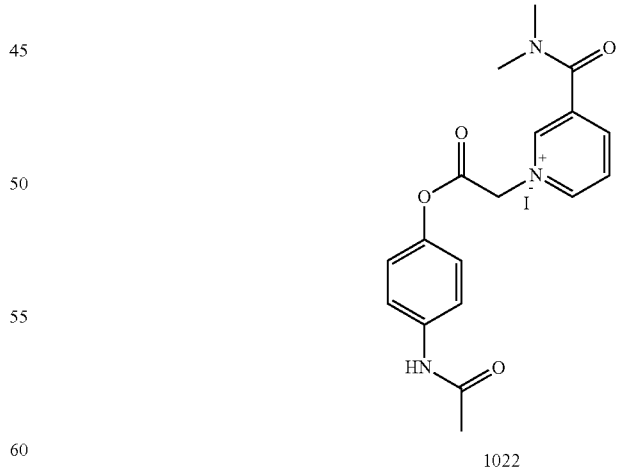

1022

Step 1:

TEA (0.28 ml, 1.98 mmol, 3.0 eq) was added to a solution of N-(4-hydroxyphenyl)acetamide, N-(4-hydroxyphenyl) ethanamide [77] (0.10 g. 0.66 mmol, 1.0 eq) of in dry THF under argon atmosphere. At 0° C., bromoacetyl chloride [78]

(0.123 g, 0.79 mmol, 1.2 equiv) was added. The reaction mixture was stirred at room temperature for 24 h. After 24 h, solvent was evaporated under vacuum and residue was taken in dichloromethane (50 ml) and washed with a 10% solution of NaHCO3 (15 ml) and then with brine (10 ml), followed by drying of the organic layer over anhydrous sodium sulfate. Evaporation of the solvents provided white solid which was purified by silica gel column chromatography (0.5% MeOH: DCM, 100-200 mesh silica) to give the product 4-acetamidophenyl 2-bromoacetate [79] (0.05 g, 28%). m/z=272

Step 2:

Sodium iodide (0.083 g, 5.52 mmol, 3.0 eq.) was added to a solution of 4-acetamidophenyl 2-bromoacetate [79] (0.050 g, 1.84 mmol, 1.0 eq.) in acetonitrile (5 ml) followed by the addition of dimethyl nicotinamide [72] (0.027 g, 1.84 mmol, 1.0 eq). The resulting reaction mixture was stirred at 40° C. for 48 h. Reaction progress was monitored by TLC. Solvent was removed tinder high vacuum to get a crude product, crude product was taken in DCM to precipitate excess of sodium iodide and sodium bromide, which was removed by filtration and filtrate was evaporated to get a yellow solid which was washed with diethyl ether (10 ml) and then dried under vacuum to yield light yellow solid, 1-(2-(4-acetamidophenoxy)-2-oxoethyl)-3-(dimethylcarbamoyl)pyridin-1-ium iodide [1022], (0.038 g, 44%). m/z: 342.

Examples 4

3-(dimethylcarbamoyl)-1-(((2-(4-isobutylphenyl)propanoyl)oxy)methyl)pyridin-1-ium mesylate [1074]

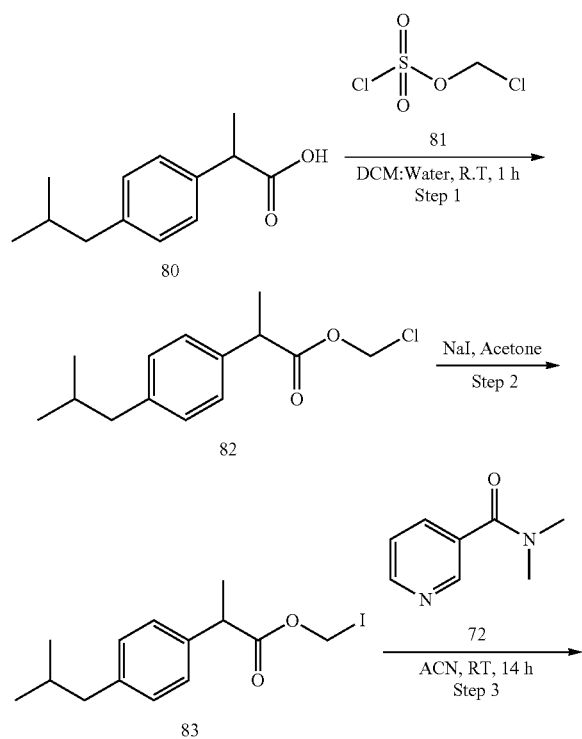

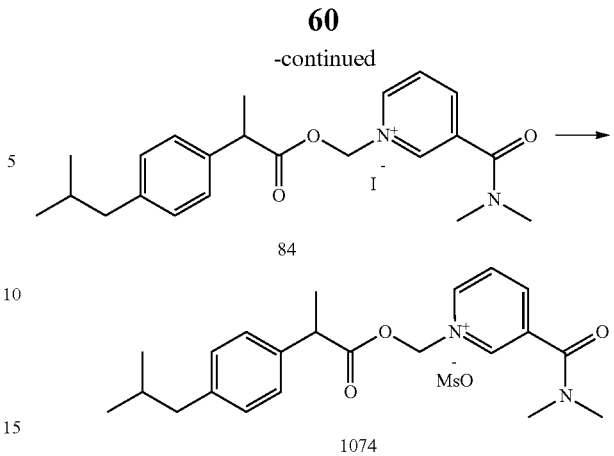

Step 1:

(RS)-2-(4-(2-methylpropyl)phenyl)propanoic acid [80] (0.1 g, 0.48 mmol, 1.0 eq) DCM (2 ml), water (2 ml), sodium bicarbonate (0.131, 1.8 mmol, 3.81 eq) and tetrabutylammonium hydrogen sulfate (0.016 g 8, 0.05 mmol, 0.1 eq) were stirred at 25° C. for 2 min. to the above reaction mixture, a solution of chloromethyl chlorosulfate [81] (0.08 ml, 0.51 mmol, 1.1 eq) in DCM (1 ml) was added dropwise and the biphasic system was stirred at RT for 1 h. The organic layer was separated and dried over anhydrous Na2SO4. Evaporation of the solvent under vacuum gave the desired product as colorless oil [82] (chloromethyl 2-(4-isobutylphenyl) propenoate), (0.06 ml, 50%).

Step 2:

Sodium iodide (0.14 g, 0.925 mmol, 4.0 eq) was added to a solution of [82] (0.06 g, 0.22 mmol, 1.0 eq) in acetone (5 ml). The resulting reaction mixture was stirred at RT for 14 h. Reaction progress was monitored by TLC. Solvent was removed under vacuum to get a crude product. Then DCM was added to the crude product to precipitate out sodium iodide which was separated by filtration, and filtrate was evaporated under vacuum to get a yellow oil [83] iodomethyl 2-(4-isobutylphenyl) propenoate (0.07 g, 86%).

Step 3:

Iodomethyl 2-(4-isobutylphenyl) propanoate [83] (0.07 g, 0.23 mmol, 1.0 eq) and dimethyl nicotinamide [72] (0.03 g, 0.22 mmol, 1.0 eq) were added in ACN (3 ml). The reaction mixture was stirred at RT for 16 h. Reaction progress was monitored by TLC. Solvent was removed under vacuum to get a crude product. The crude product obtained was triturated with diethyl ether (2×5 ml) to give the desired product [84], 3-(dimethylcarbamoyl)-1-(((2-(4-isobutylphenyl)propanoyl)oxy)methyl)pyridin-1-ium iodide (0.045 g, 60%).

Step 4:

To a stirred solution of 3-(dimethylcarbamoyl)-1-(((2-(4-isobutylphenyl)propanoyl)oxy)methyl)pyridin-1-ium iodide [84] (0.03 g, 0.006 mmol, 1.0 eq) in ACN (2 ml) was added silver(I) methanesulfonate (0.012 g, 0.006 mmol, 1.0 eq) at RT. The reaction mixture was stirred at RT for 2 h. The reaction was filtered to get rid of silver iodide. Filtrate was concentrated under vacuum, which was triturated with dry ether (2×5 ml), ether removed by decantation and product dried under vacuum to get the desired product 3-(dimethylcarbamoyl)-1-(((2-(4-isobutylphenyl)propanoyl)oxy)methyl)pyridin-1-ium iodide mesylate [1074] (0.025 g, 90%) as pale yellow solid. m/s: 495

Compound no. 1008, 1011-16, 1018-22, 1024, 1025, 1028, 1047-1049 were prepared by the procedure described in example 4.

Example 5

Synthesis of 1-(((isopropylcarbamoyl)oxy)methyl)-3-(2-((2-methyl-5-((3-(4-methyl-1H-imidazol-3-ium-1-yl)-5-(trifluoromethyl)phenyl)carbamoyl)phenyl)amino)pyrimidin-4-yl)pyridin-1-ium methanesulfonate [1032]

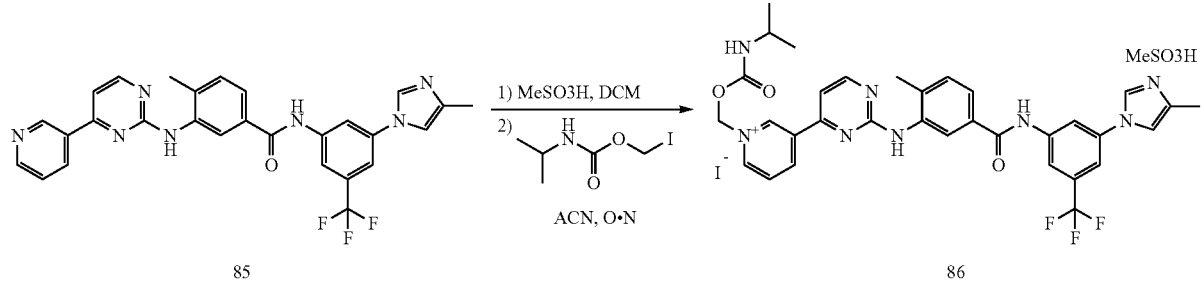

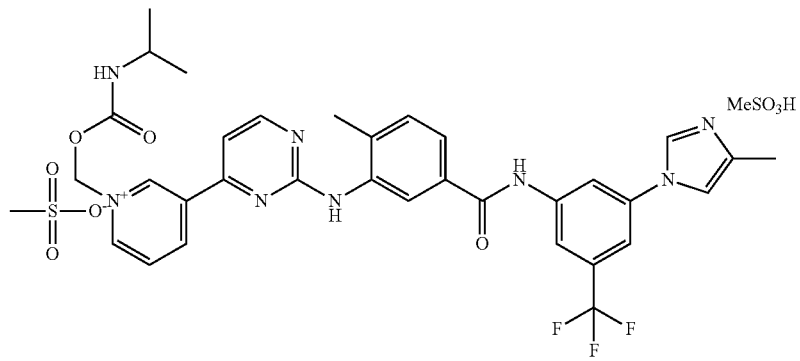

Step 1:—

To stirred solution of 4-methyl-N-(3-(4-methyl-1H-imidazol-1-yl)-5-(trifluoromethyl)phenyl)-3-((4-(pyridin-3-yl)pyrimidin-2-yl)amino)benzamide [85] (0.09 g, 0.00017 mmol, 1.0 eq) in DCM (5 ml), was added at 0° C. Methane sulfonic acid (0.016 g, 0.00017 mmol, 1.0 eq). The reaction mixture was stirred at RT for 30 min. The organic solvent was evaporated and ACN (5 ml) was added to the residue obtained. Iodomethyl isopropylcarbamate (0.041 g, 0.00017 mmol, 1.0 eq) was added. Reaction mixture was heated at 50° C. for overnight, organic solvent was evaporated to get crude material, crude product dissolved in distilled water (5 mL) & washed with DCM, aqueous layer was lyophilized to yield 1-(((isopropylcarbamoyl)oxy)methyl)-3-(2-((2-methyl-5-((3-(4-methyl-1H-imidazol-1-yl)-5-(trifluoromethyl)phenyl)carbamoyl)phenyl)amino)pyrimidin-4-yl)pyridin-1-ium iodide methane sulfonic acid salt [86] (0.09 g, 90%) as yellow solid. Mass: m/z at 646

Step 2:—

To a stirred solution of 1-(((isopropylcarbamoyl)oxy)methyl)-3-(2-((2-methyl-5-((3-(4-methyl-1H-imidazol-1-yl)-5-(trifluoromethyl)phenyl)carbamoyl)phenyl)amino)pyrimidin-4-yl)pyridin-1-ium iodide methane sulfonic acid salt (861 (0.04 g, 0.00004 mmol, 1.0 eq) in ACN:Water (2:2 mL) was added silver(I) methanesulfonate (0.00093 gm, 0.00004 mmol, 1.0 eq) at RT. The reaction mixture was stirred at RT for 1 h. The reaction was filtered to get rid of silver iodide. Filtrate was lyophilized to get the desired product 1-(((isopropylcarbamoyl)oxy)methyl)-3-(2-((2-methyl-5-((3-(4-methyl-1H-imidazol-1-yl)-5-(trifluoromethyl)phenyl)carbamoyl)phenyl)amino)pyrimidin-4-yl)pyridin-1-iumdimesylate [1032], (0.021 g, 55%) as light yellow solid. Mass: m/z at 646.

Compound no. 1032-35 were prepared by the procedure described in example 6

Example 6

Synthesis of 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropoxycarbonyl)oxy)methyl)-1-methylpiperazin-1-ium iodide [1039]

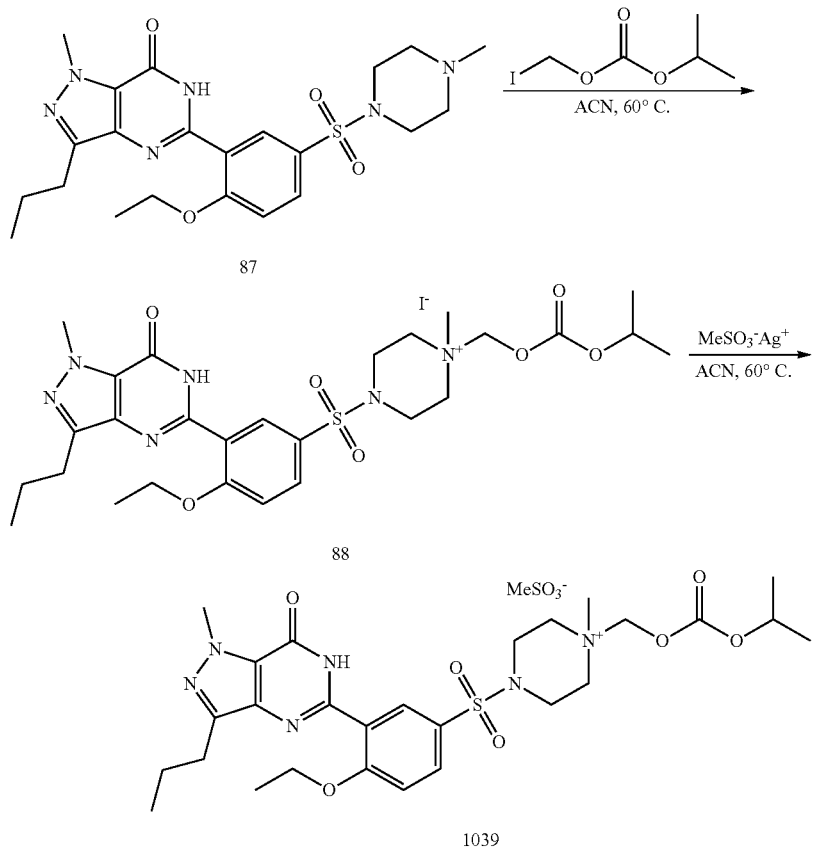

Step 1:—

To a stirred solution of 1-[4-ethoxy-3-(6,7-dihydro-1-methyl-7-oxo-3-propyl-1H-yrazolo[4,3-d]pyrimidin-5-yl)phenylsulfonyl]-4-methylpiperazine1-[4-ethoxy-3-(6,7-dihydro-1-methyl-7-oxo-3-propyl-1H-pyrazolo[4,3-d]pyrimidin-5-yl)phenylsulfonyl]-4-methylpiperazine) [87], 0.107 g, 0.225 mmol, 1.0 eq) in ACN (15 ml) was added iodomethyl isopropylcarbonate (0.085 g, 0.348 mmol, 1.54 eq) at RT. The reaction was stirred at 60° C. for 3-4 h. ACN was removed under vacuum; product triturated with ether to get 4-((4-ethoxy-3-(1-methyl-7-oxo-3-propyl-6,7-dihydro-1H-pyrazolo[4,3-d]pyrimidin-5-yl)phenyl)sulfonyl)-1-(((isopropoxycarbonyl)oxy)methyl)-1-methylpiperazin-1-ium iodide as off white solid ([88], 0.137 g, 84%).

Step 2:—

To a solution of 4-((4-ethoxy-3-(1-methyl-7-oxo-3-propyl-6,7-dihydro-1H-pyrazolo[4,3-d]pyrimidin-5-yl)phenyl)sulfonyl)-1-(((isopropoxycarbonyl)oxy)methyl)-1-methylpiperazin-1-ium iodide ([88], 0.137 g, 0.190 mmol, 1.0 eq) in ACN (7 mL) at RT was added silver salt of methane sulphonate (0.037 g, 0.182 mmol, 0.96 eq). The reaction was stirred at RT for 20 min and filtered through 0.45µ nylon filter, ACN evaporated and compound triturated with ether and then n-penatane to get 4-((4-ethoxy-3-(1-methyl-7-oxo-3-propyl-6,7-dihydro-1H-pyrazolo[4,3-d]pyrimidin-5-yl)phenyl)sulfonyl)-1-(((isopropoxycarbonyl)oxy)methyl)-1-methylpiperazin-1-ium methanesulfonate [1039] as off white solid (0.0724 g, 55%). Mass=m/z at 591.

Compound no. 1036-43 were prepared by the procedure described in example 6.

Example 7

Synthesis of 3-carbamoyl-1-(((2,6-diisopropylphenoxy)carbonyloxy)methyl)pyridinium mesylate [1003]

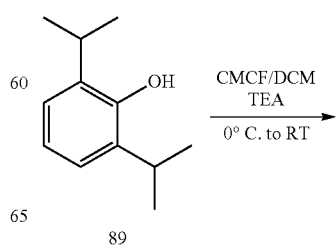

65

-continued

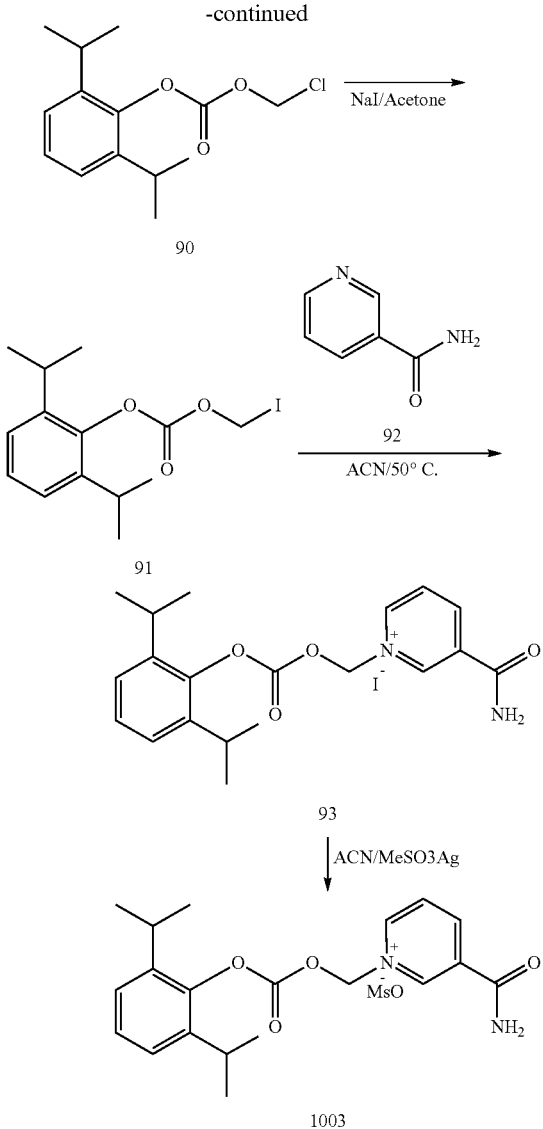

Step 1:—

To a solution of Propofol [89] (0.1 gm, 0.53 mmol, 1 eq) in 5 ml dichloromethane at 0° C., triethyl amine was added and stirred the resulting solution at 0° C. for 20 min. After stirring for 20 min at 0° C., chloromethyl chloroformate (0.12 ml, 0.84 mmol, 1.5 eq) was added dropwise and stirred for 2 hrs at 0° C. and allowed to stirred at RT for 2 Hrs, During the reaction progress solution was turned into a white precipitate. The reaction progress was monitored by TLC. The reaction mixture was diluted with dichloromethane (50 ml), washed with water (15 ml), 10% solution of NaHCO3 (15 ml), dil HCl (10 ml), followed by brine (10 ml), and the organic layer dried over anhydrous sodium sulfate. Evaporation of the solvents under vacuum gave the crude product chloromethyl (2,6-diisopropylphenyl) carbonate [90] as a colourless gel. (0.012 g, 80%). m/z: 271

Step 2:

Sodium iodide (0.2 g, 1.3 mmol 3.0 eq) was added to a solution of chloromethyl (2,6-diisopropylphenyl) carbonate [90] (0.120 g, 0.44 mmol, 1.0 eq) in acetone. The resulting reaction mixture was stirred at RT for 5 Hrs. Reaction progress was monitored by TLC. The reaction mixture was

66 filtered through filter paper to remove formed sodium chloride during reaction. Then solvent was evaporated and passed through a bed of silica (mesh 100-200). The silica bed was washed several times with dichloromethane and fractions collected and evaporated under vacuum to yield the desired product 2,6-diisopropylphenyl (iodomethyl) carbonate [91], (0.109 gm, 90%). m/z: 363

Step 3:

Nicotinamide [92] (0.02 g, 0.16 mmol, 1.0 eq) was added to a solution of 2,6-diisopropylphenyl (iodomethyl) carbonate [91] (0.07 g, 0.16 mmol, 1.0 eq) in dry acetonitrile (2 ml) under argon atmosphere. The resulting reaction mixture was stirred at 50° C. for 20 Hrs. Reaction progress was monitored by TLC. Solvent was removed under vacuum to get a crude product. The crude product obtained was triturated with diethyl ether (10 ml×2) to give the desired product, 3-carbamoyl-1-((((2,6-diisopropylphenoxy)carbonyl)oxy) methyl)pyridin-1-ium iodide [93] as a yellow solid (0.050 gm, 65%). m/z: 358.

Step 4:

To a stirred solution of, 3-carbamoyl-1-((((2,6-diisopropylphenoxy) carbonyl)oxy)methyl)pyridin-1-ium iodide [93] (0.045 g, 0.09 mmol, 1.0 eq) in ACN (2 ml) was added silver(I) methanesulfonate (0.019 g, 0.09 mmol, 1.0 eq) at RT. The reaction mixture was stirred at RT for 2 h. The reaction was filtered to get rid of silver iodide. Filtrate was concentrated under vacuum, which was triturated with dry ether (2×5 ml), ether removed by decantation and product dried under vacuum to get the desired product 3-carbamoyl-1-((((2,6-diisopropylphenoxy)carbonyl)oxy)methyl)pyridin-1-ium iodide mesylate [1003] (0.035 g, 83%) as light yellow solid. m/z: 358.

Example 8

Synthesis of (methylsulfonyl)-1-oxidane, 1-(((2,6-diisopropylphenoxy) carbonyl)oxy)methyl-3-(methylcarbamoyl)pyridin-1-ium salt [1002]

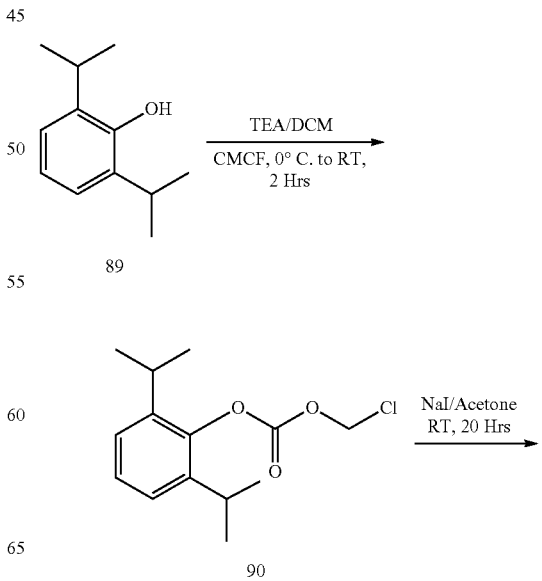

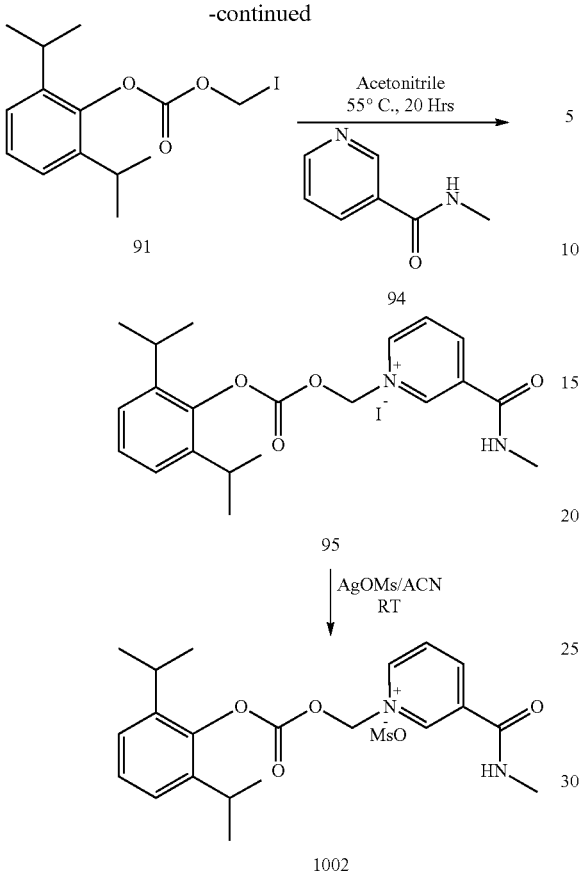

Step 1:
Triethyl amine (4.0 ml, 0.028 mmol, 2.0 eq) was added to a solution 2,6-diisopropylphenol [89] (2.5 g, 0.014 mmol, 1.0 eq) in dry DCM (30 ml) under nitrogen atmosphere at 0° C. followed by addition of chloromethyl chloroformate (1.54 ml, 0.017 mmol, and 1.25 eq). The reaction mixture was stirred at 0° C. for 2 h and reaction progress was monitored by TLC. After 2 h, the reaction mixture was diluted with dichloromethane (250 ml), washed with water (100 ml), 10% solution of $NaHCO_3$ (150 ml), dil HCl (100 ml), followed by brine (100 ml). The organic layer thus obtained was dried over anhydrous sodium sulfate. Evaporation of the solvents under vacuum provided crude product, which was purified using silica gel column chromatography (100-200 mesh) using cyclohexane:dichloromethane (3%) as eluent to obtain colourless liquid 190) (3.1 g, 83%). m/z: 271

Step 2:
Sodium iodide (7.0 g, 0.046 mol, 4.0 eq) was added to a solution of chloromethyl (2,6-diisopropylphenyl) carbonate [90] (3.1 g, 0.012 mol, 1.0 eq) in acetone. The resulting reaction mixture was stirred at room temperature for 20 hrs. The reaction progress was monitored by TLC. The reaction mixture was then filtered off and residue was washed with excess of acetone. Filtrate was evaporated and passed through a bed of silica (mesh 100-200). The compound was eluted with cyclohexane to yield product as a colourless liquid [91] (3.3 g, 80%). m/z: 363

Step 3:
N-methylnicotinamide [94] (0.68 g, 0.0049 mol, 0.9 eq) was added to a solution of iodomethyl (2,6-diisopropylphenyl) carbonate [91] (2.0 g, 0.0055 mol, 1.0 eq) in dry acetonitrile (20 ml) under nitrogen atmosphere. The resulting reaction mixture was stirred at 50° C. for 20 hrs. The reaction progress was monitored by TLC. Then solvent was removed under vacuum to get a crude product as a dark brown solid. The crude product was dissolved in DCM and then triturated with diethyl ether to give the desired product 195) as a yellow powder (2.1 g, 78%). m/z: 371

Step 4:
To a stirred solution of 1-((((2,6-diisopropylphenoxy)carbonyl)oxy)methyl)-3-(methylcarbamoyl)pyridin-1-ium iodide (951 (0.035 g, 0.00007 mol, 1.0 eq) in ACN (2 ml) was added silver(I) methanesulfonate (14 mg, 0.00007 mol, 1.0 eq) at RT. The reaction mixture was stirred at RT for 30 mins. The reaction was filtered to get rid of silver iodide. Filtrate was concentrated under vacuum, which and triturated with diethyl ether to afford product as a colourless solid [1002] (0.030 g, 95%). m/z: 371

Compound no. 1001, 1004, 1031, 1060, 1061 were prepared by the procedure described in Example 8.

Example 9

Synthesis of (methylsulfonyl)-11-oxidane, 3-((2,6-diisopropylphenoxy) carbonyl)-1-((((2,6-diisopropylphenoxy)carbonyl)oxy)methyl)pyridin-1-ium salt [1069]

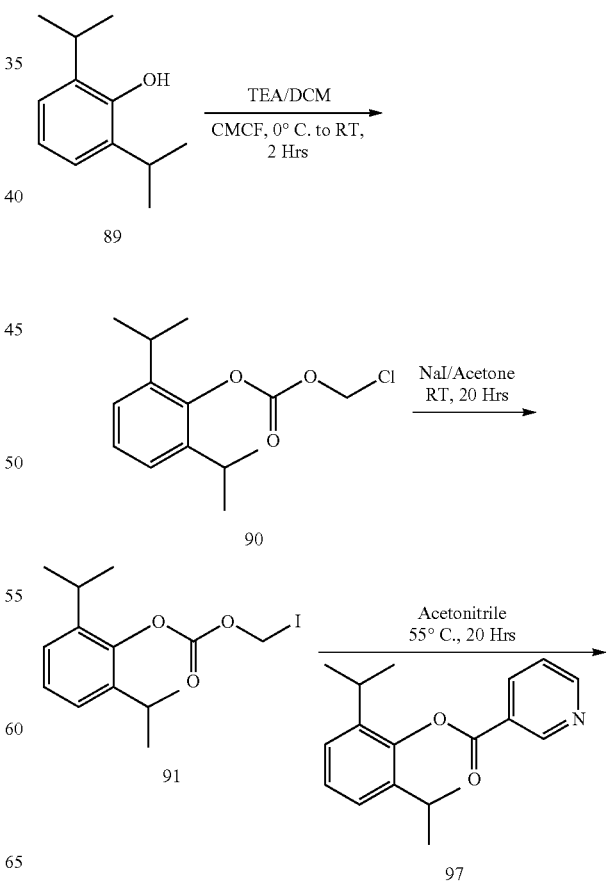

69

-continued

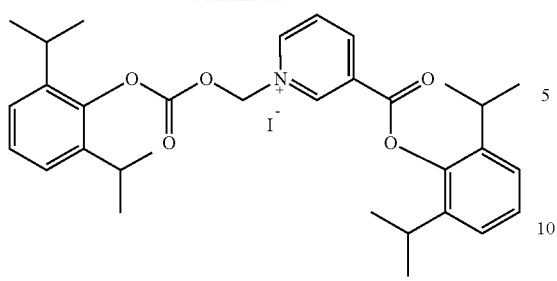

98

↓ AgOMs/ACN
RT

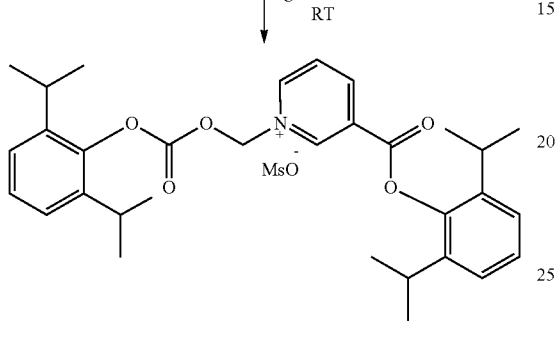

1069

Compound [1069] was prepared by the procedure described in example 8.

Example 10

Synthesis of 2-(((2,6-diisopropylphenoxy)carbonyl)oxy)-N,N,N-trimethyl ethan-1-aminium methanesulfonate [1070]

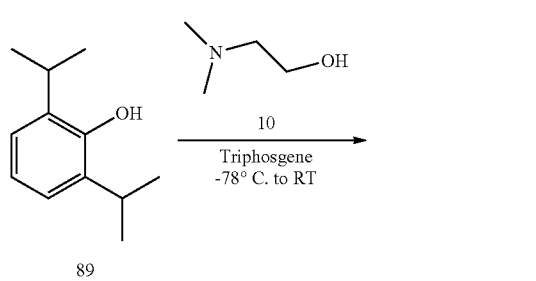

89

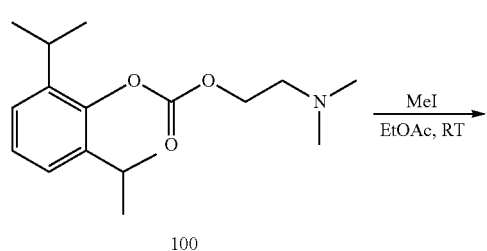

100

70

-continued

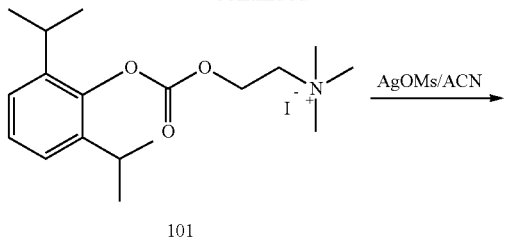

101

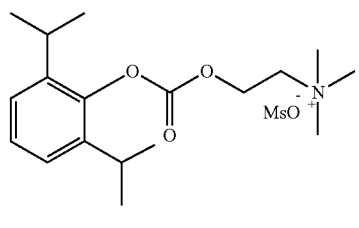

1070

Step 1:

Triphosgene (0.145 gm, 0.00049 mol, 0.35 eq) was dissolved in 10 ml dichloromethane and cooled to −78° C. Propofol [89] (0.25 gm, 0.0014 mol, 1.0 eq) was dissolved in 7 ml dichloromethane and pyridine (0.44 gm, 0.0056 mol, 4.0 eq) and then added to the triphosgene solution. The reaction was slowly warmed to room temperature and stirred for additional 2 hrs. The reaction mixture was cooled back to −78° C. followed by addition of dimethyl amino ethanol (0.11 gm, 0.00126 mol, 0.9 eq) predissolved in 3 ml dichloromethane. The reaction mixture slowly warmed to room temperature and stirred for another 1 hr. Reaction mixture was diluted with DCM (100 ml) and washed successively with water, sat.NaHCO$_3$ and brine solution. Organic layer was dried over Na2SO4, and evapourated to yield colourless gel of [100] (0.38 gm, 92%). m/z:—294

Step 2:

To a solution of 2,6-di-isopropylphenyl (2-(dimethylamino)ethyl) carbonate [100] (0.05 gm, 0.00017 mol, 1.0 eq) in 10 ml ethyl acetate was added methyl iodide (0.05 ml, 0.00034 mol, 2.0 eq). The solution was stirred at room temperature for 1 hr leading to formation of white precipitates. The precipitates were filtered off and washed with diethyl ether to remove any leftover methyl iodide. The precipitate was dried to yield product as colourless solid of [101] (0.06 gm, 81%). m/z:—308

Step 3:

To a stirred solution of 2-(((2,6-diisopropylphenoxy)carbonyl)oxy)-N,N,N-trimethylethan-1-aminium iodide [10] (0.030 g, 0.00007 mol, 1.0 eq) in ACN (2 ml) was added silver(I) methanesulfonate (0.014 g, 0.00007 mol, 1.0 eq) at RT. The reaction mixture was stirred at RT for 30 min. The reaction was filtered to get rid of silver salt. Filtrate was concentrated under vacuum and re-dissolved in dichloromethane followed by filtration leading to separation of solid material. Filtrate was evaporated under vacuum to desired product as a colourless solid [1070] (0.022 g, 78%). m/z: 308

Compound no. 1062 and 1063 were prepared by the procedure described in example 10.

Example 11

(S)-1-((((2-(carboxymethyl)-2,4-dimethylpentyl)carbamoyl)oxy)methyl)-3-(dimethylcarbamoyl)pyridin-1-ium methanesulfonate [1076]

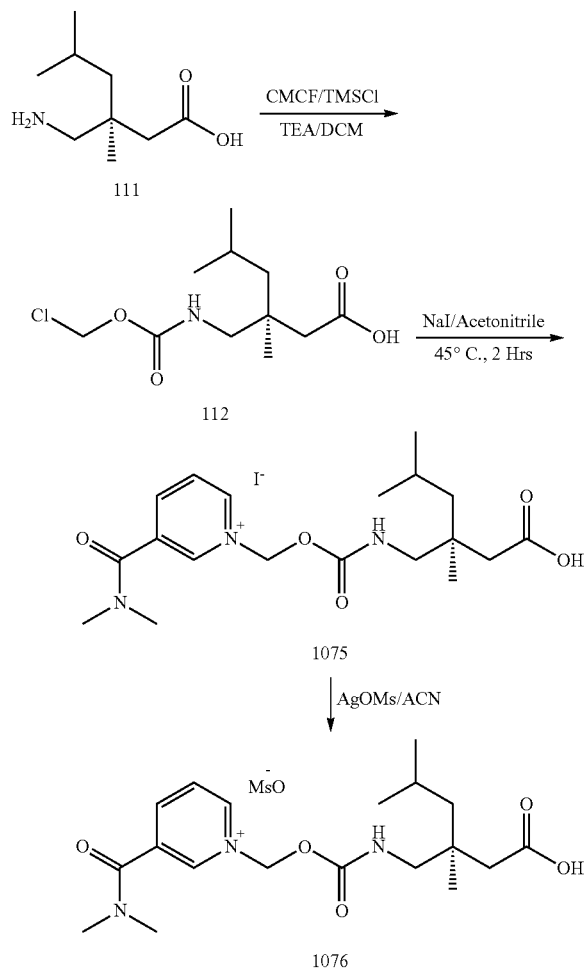

Step 1:—

To a stirred suspension of (S)-3-(aminomethyl)-3,5-dimethylhexanoic acid [111] (0.4 gm, 2.5 mmol, 1 eq) in 50 ml of DCM at 0° C. was added TEA and stirred for 10 min. To this TMSCl was added and again stirred it for 1 hrs at same temperature and then at rt for 15 min. Then it was cooled down back to 0° C. and CMCF was added dropwise and stirred the resulting reaction mixture at RT for overnight. The progress of the reaction was monitored by TLC. The resulting silyl ester was then converted to acid by quenching with aq. 10% citric acid solution and extracted the compound by DCM (100 ml×2). DCM layer was then washed with brine solution and crude product was purified by silica gel chromatography (100-200 mesh size) and eluted the compound by MeOH:DCM (2%) to yield product (S)-3-(((((chloromethoxy)carbonyl)amino)methyl)-3,5-dimethylhexanoic acid [112] as a colourless gel (0.35 gm, 55%), M+1:—266

Step 2:—

To a solution of (S)-3-(((((chloromethoxy)carbonyl)amino)methyl)-3,5-dimethylhexanoic acid [112] (0.1 gm, 3.0 mmol, 1.0 eq) in acetonitrile sodium iodide (0.050 gm, 3.3 mmol, 1.1 eq) and Dimethyl nicotinamide (0.057 gm, 3.0 mmol, 1.0 eq) was added and resulting reaction mixture was heated at 45° C. for 2 Hrs. The progress of the reaction was monitored by TLC. It was then cooled to RT and filtered off the solid as a NaCl and filtrate was evaporated to get crude residue which was washed successively with DCM. Then residue was dissolved in mixture of DCM:MeOH (9:1) and triturated it with diethyl ether to yield (S)-1-((((2-(carboxymethyl)-2,4-dimethylpentyl)carbamoyl)oxy)methyl)-3-(dimethylcarbamoyl)pyridin-1-ium iodide [1075] as a yellow solid (0.08 gm, 42%). M+ peak:—380

Step 3:—

To a stirred solution of (S)-1-((((2-(carboxymethyl)-2,4-dimethylpentyl)carbamoyl)oxy)methyl)-3-(dimethylcarbamoyl)pyridin-1-ium iodide [1075] (0.06 gm, 0.12 mmol, 1.0 eq) in ACN (2 ml) was added silver(I) methanesulfonate (0.025 gm, 0.12 mol, 1.0 eq) at RT. The reaction mixture was stirred at RT for 30 min. The reaction was filtered to get rid of silver salt. Filtrate was concentrated under vacuum and re-dissolved in dichloromethane followed by filtration leading to separation of solid material. Filtrate was evaporated under vacuum to desired product (S)-1-((((2-(carboxymethyl)-2,4-dimethylpentyl)carbamoyl)oxy)methyl)-3-(dimethylcarbamoyl)pyridin-1-ium methanesulfonate [1076] as a colourless solid (0.03 gm, 54%). M+ peak: 380

Compound no. 1044, 1045, 1052, 1054, 1055, 1057 and 1058 were prepared by the procedure described in example 11.

Example 12

3-carbamoyl-1-(((1-cyclopropyl-4-methyl-6-oxo-6,11-dihydro-5H-dipyrido[3,2-b:2',3'-e][1,4]diazepine-5-carbonyl)oxy)methyl)pyridin-1-ium methanesulfonate[1073]

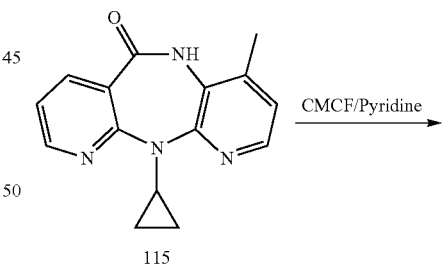

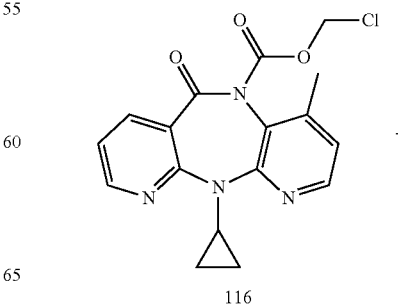

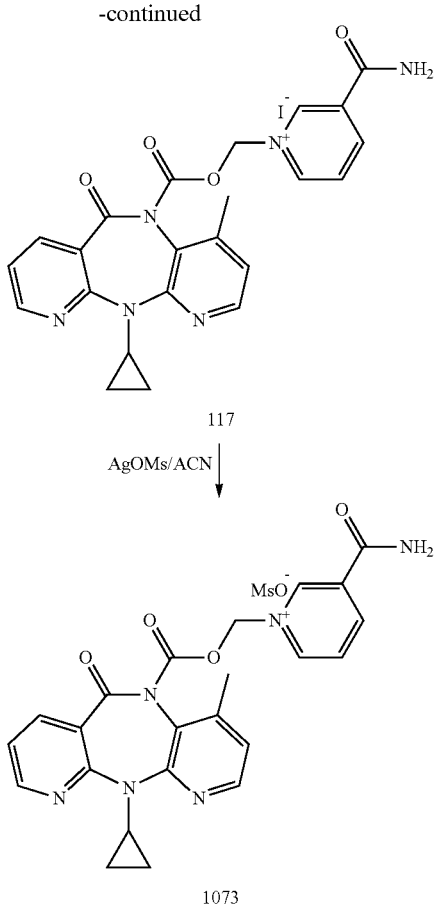

Step 1:—

To a cooled solution of CMCF (0.146 ml, 1.69 mmol, 1.5 eq) in DCM at 0° C. pyridine (0.178 ml, 1.69 mmol, 1.5 eq) was added and stirred it for 10 min. Then 11-cyclopropyl-4-methyl-5,11-dihydro-6H-dipyrido[3,2-b:2',3'-e][1,4]diazepin-6-one[115] (0.3 gm, 1.1 mmol, 1.0 eq) was added and stirred the resulting reaction mixture was refluxed to 50° C. for 4 hrs. The reaction was monitored by TLC. Reaction was quenched by water and extracted the compound by DCM (100 ml), dried over Na₂SO₄ and evaporated to yield crude product as a gel which was purified by using column chromatography over silica gel (100-200 mesh size) and eluted the compound by MeOH:DCM (1%) to yield chloromethyl 11-cyclopropyl-4-methyl-6-oxo-6,11-dihydro-5H-dipyrido[3,2-b:2',3'-e][1,4]diazepine-5-carboxylate[116] as a light brown solid (0.31 gm, 75%). M+1 peak at 359.

Step 2:—

To a solution chloromethyl 11-cyclopropyl-4-methyl-6-oxo-6,11-dihydro-5H-dipyrido[3,2-b:2',3'-e][1,4]diazepine-5-carboxylate [16] (0.1 gm, 2.7 mmol, 1.0 eq) in acetonitrile sodium iodide (0.08 gm, 5.4 mmol, 2.0 eq) and Dimethyl nicotinamide (0.041 gm, 2.7 mmol, 1.0 eq) was added and resulting reaction mixture was heated at 50° C. for overnight. The progress of the reaction was monitored by TLC. It was then cooled to RT and filtered off the solid as a NaCl and filtrate was evaporated to yielded crude residue which was washed successively with DCM. Then residue was triturated it with diethyl ether to yield 3-carbamoyl-1-(((11-cyclopropyl-4-methyl-6-oxo-6,11-dihydro-5H-dipyrido[3,2-b:2',3'-e][1,4]diazepine-5-carbonyl)oxy)methyl)pyridin-1-ium iodide [117] as a white solid (0.10 gm, 78%). M+ peak:—445.

Step 3:—

To a stirred solution of 3-carbamoyl-1-(((1 1-cyclopropyl-4-methyl-6-oxo-6,11-dihydro-5H-dipyrido[3,2-b:2',3'-e][1,4]diazepine-5-carbonyl)oxy)methyl)pyridin-1-ium iodide [117] (0.085 gm, 0.145 mmol, 1.0 eq) in ACN (2 ml) was added silver(1) methanesulfonate (0.029 gm, 0.145 mol, 1.0 eq) at RT. The reaction mixture was stirred at RT for 30 min. The reaction was filtered to get rid of silver salt. Filtrate was concentrated under vacuum and washed with diethyl ether to yield desired product 3-carbamoyl-1-(((11-cyclopropyl-4-methyl-6-oxo-6,11-dihydro-5H-dipyrido[3,2-b:2',3'-e][1,4]diazepine-5-carbonyl)oxy)methyl)pyridin-1-ium methanesulfonate [1073] as a colourless solid (0.03 gm, 54%). M+ peak: 445.

Compound no. 1071-73 was prepared by the procedure described in example 12.

Example 13

Rat and Human Plasma Conversion Study of Compound 1004

The stock solution of compound 1004 was prepared at a concentration of 10 mg/ml in DMSO. To 450 ul human/rat plasma taken in Eppendorf tube, compd. 1004 was added to get a final concentration of 200 ug/ml. The incubation temperature was 37° C. 50 ul of sample was taken out at each time point and reaction was stopped with 200 ul of 100% acetonitrile. The supernatants were analyzed by HPLC. For HPLC analysis of compd. 1004, Agilent Eclips, XDB-C 18 (4.6×150 mm) column and mobile phase 0.1% TFA in MQ water and Acetonitrile was used. Flow rate was maintained at 1.5 ml/min. and injection volume of 10 ul. The standard calibration curve was generated using SPR10820 in acetonitrile at different concentrations. The maximum concentration of 71.5 ug/ml of Propofol was expected from 200 ug/ml of compd. 1004.

Example 14

General Anesthetic Activity of Propofol Novel Drug Compound 1004

The general anesthetic activity of Propofol novel drug compound 1004 was evaluated in rats. All animal experiments were performed as per CPCSEA guidelines. The studies were carried out in Sprague Dawley (SD) rat in the weight range 120-1808 by intravenous tail vein dosing over a period of 10 seconds. The formulations of the compound 1004 for IV dosing in rats were prepared in pre-mix PEG400 and saline. Formulations of 1004 equivalent to 5 mpk (14 mpk of compd. 1004) and 7.5 mpk (equivalent to 21 mpk of compound 1004) of parent drug Propofol were prepared in 15% PEG400 and 85% normal saline. The monitoring of distinguishable levels of sedation was started during the dosing period and continued till animals regained consciousness. The onset, duration of sleep and recovery time was recorded. (Table2).

TABLE 2

General Anesthetic Activity of Propofol and propofol novel drug compound no. 1004

| Compd | Vehicle | Propofol Eq. (mpk) | General Anesthesia (GA) | Duration | Recovery |
|---|---|---|---|---|---|
| 1004 | 15% PEG400, 85% NS | 7.5 | After 1 min | 3'45" | Complete |
| Propofol | 15% PEG400, 85% NS | 7.5 | No GA | 4' | Complete |

PK Protocol

Female Sprague Dawley (SD) rats 3 per group after overnight fasting were dosed orally (via gavage) with imatinib and its novel drugs in distilled water (5 ml/kg) at a dose level of 3 mg/kg. Blood was collected by serial bleeding at 0.16 h, 0.5 h, 1 h, 2 h, 4 h, 6 h, 8 h and 24 h in heparinized tubes. Blood samples were centrifuged at 10,000 rpm for 10 min. at 4° C. to obtain the plasma, which were aspirated into separate labeled tubes and stored at −80° C. 400 ng/ml of Verapamil in acetonitrile was used as the drug extraction solvent for extracting drug from plasma. Extraction solvent was added to plasma was vortexed and shaken on shaker for 10 min, centrifuged at 10000 rpm for 10 min at 4° C. Supernatant was kept for analysis. Acetonitrile and plasma calibration curves were generated and percentage of drug recovery from plasma determined. Quantitative analysis was done by liquid chromatography tandem mass spectrometry using multiple reaction monitoring (AP13000 LC-MS/MS). $C_{max}$, $T_{max}$, AUC and $t_{1/2}$ were calculated using Graph Pad PRISM version 5.04.

TABLE 3

PK Parameters for certain exemplary compounds

| Compound Number | $T_{max}$ (hr) | $C_{max}$ (uM) | AUC (uM) | $t_{1/2}$ (hr) |
|---|---|---|---|---|
| Sildenafil | 0.08 | 3084 | 1451 | 2.67 |
| 1049 | 0.25 | 232 | 146 | 2.46 |
| 1046 | 0.5 | 434 | 438 | 2.44 |
| 1047 | 0.59 | 301 | 285 | 2.42 |
| 1045 | 0.83 | 558 | 610 | 2.08 |
| 1052 | 1.83 | 134 | 261 | 2.77 |

* Triplicate in rats dosed at 10 mpk

Based on Table 3, it may be clearly seen that the novel novel compounds of the present invention have improved pharmacokinetic properties in comparison to that of the unnovel drugs.

The invention claimed is:

1. A method for modifying the properties of a drug, comprising
   (i) converting the DRUG to DRUG-O—C($R^1R^2$)G
   (ii) reacting the DRUG-O—C(G(R1R2)G with

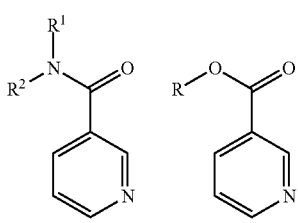

to give [Y—O—X]$^+$G$^-$, wherein:
Y is the drug linked to through a carbonyl (—CO—), oxycarbonyl (—O—CO—), or amine carbonyl (—NR—CO—)
X is selected from

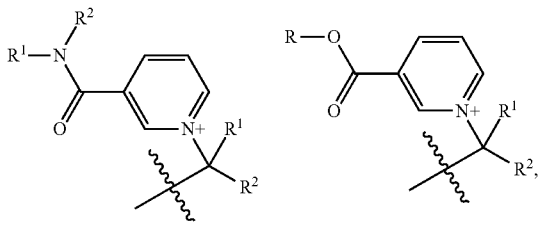

R, $R^1$ and $R^2$ are independently H; $C_1$-$C_8$ straight, or branched chain alkyl; $C_1$-$C_8$ straight or branched chain alkyl substituted with 1-3 heteroatoms selected from O, N, S, SO, or $SO_2$; 3-7 membered cycloalkyl; 3-7 membered cyclo alkyl that has been substituted with 1-3 heteroatoms selected from O, N, S, SO, or $SO_2$ and/or lower alkyl; straight or branched alkyl, alkoxy; alkaryl, aryl, heteroaryl, or alkheteroaryl; or is independently part of 3-7 membered ring optionally containing additional 1-2 heteroatoms selected from, O, N, S, SO, $SO_2$ and optionally substituted with alkoxy, F or Cl; and G− is selected from iodide, chloride, bromide, mesylate, tosylate and tetra fluoroborate.

2. The method of claim 1, wherein the modified drug compound is selected from the group consisting of:
   i. 1-(((2,6-diisopropylphenoxy)carbonyloxy)methyl)-3-(dimethylcarbamoyl)pyridinium mesylate;
   ii. 1-(((2,6-diisopropylphenoxy)carbonyloxy)methyl)-3-(methylcarbamoyl)pyridinium mesylate;
   iii. 3-carbamoyl-1-(((2,6-diisopropylphenoxy)carbonyloxy)methyl)pyridinium mesylate;
   iv. 1-(((2,6-diisopropylphenoxy)carbonyloxy)methyl)-3-(methylcarbamoyl)pyridinium iodide;
   v. (E)-3-(dimethylcarbamoyl)-1-(((2-methoxy-4-((8-methylnon-6-enamido)methyl)phenoxy)carbonyloxy)methyl)pyridinium iodide;
   vi. (E)-3-(dimethylcarbamoyl)-1-(((2-methoxy-4-((8-methylnon-6-enamido)methyl)phenoxy)carbonyloxy)methyl)pyridinium mesylate;
   vii. 3-(dimethylamino)-1-(((4-((1E,4Z,6E)-5-hydroxy-7-(4-hydroxy-3-methoxyphenyl)-3-oxohepta-1,4,6-trienyl)-2-methoxyphenoxy)carbonyloxy)methyl)pyridinium iodide;

viii.

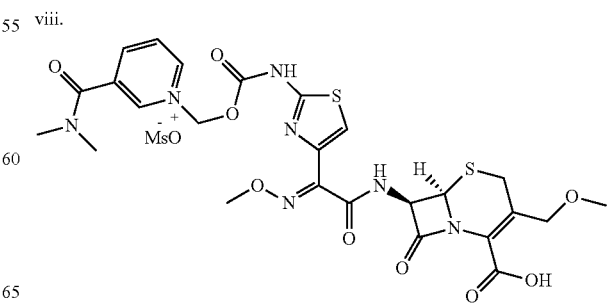

ix. 3-(dimethylcarbamoyl)-1-((2-(4-isobutylphenyl)propanoyloxy)methyl)pyridinium iodide;
x. 1-((2-acetoxybenzoyloxy)methyl)-3-carbamoylpyridinium iodide;
xi. 1-((2-acetoxybenzoyloxy)methyl)-3-(methylcarbamoyl)pyridinium iodide;
xii. 1 ((2-acetoxybenzoyloxy)methyl)-3-(dimethylcarbamoyl)pyridinium iodide;
xiii. 1-((2-acetoxybenzoyloxy)methyl)-3-carbamoylpyridinium mesylate;
xiv. 1-((2-acetoxybenzoyloxy)methyl)-3-dimethylcarbamoyl)pyridinium mesylate;
xv. 1-((2-acetoxybenzoyloxy)methyl)-3-(methylcarbamoyl)pyridinium mesylate;

xvi.

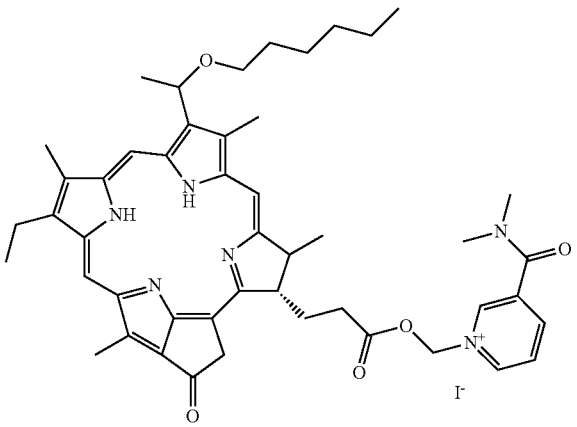

xvii.

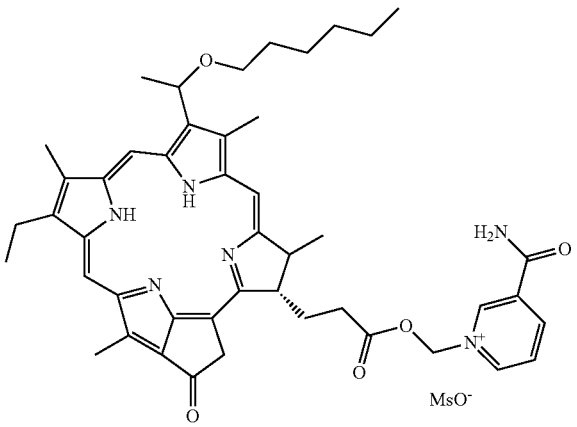

xviii. 3-carbamoyl-1-((2-(1-(4-chlorobenzoyl)-5-methoxy-2-methyl-1H-indol-3-yl)acetoxy)methyl)pyridinium iodide;
xix. 1-((2-(1-(4-chlorobenzoyl)-5-methoxy-2-methyl-1H-indol-3-yl)acetoxy)methyl)-3-(dimethylcarbamoyl)pyridinium iodide;
xx. 1-((2-(1-(4-chlorobenzoyl)-5-methoxy-2-methyl-1H-indol-3-yl)acetoxy)methyl)-3-(dimethylcarbamoyl)pyridinium mesylate;
xxi. 1-((2-(2-(2,6-dichlorophenylamino)phenypacetoxy)methyl)-3-(dimethylcarbamoyl)pyridinium iodide;
xxii. 1-(2-(4-acetamidophenoxy)-2-oxoethyl)-3-(dimethylcarbamoyl)pyridin-1-ium iodide
xxiii. 1-((((((1S,2R)-1-benzamido-3-(((2aR,4S,4aS,6R,9S,11S,12S,12aR,12bS)-6,12b-diacetoxy-12-(benzoyloxy)-4-(((3-(dimethylcarbamoyl)pyridin-1-ium-1-yl)methoxy)carbonyl)oxy)-11-hydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)oxy)methyl)-3-(dimethylcarbamoyl)pyridin-1-ium diiodide;
xxiv. 1-(((((6R,7R)-7-((E)-2-(2-aminothiazol-4-yl)-2-(methoxyimino)acetamido)-3-(methoxymethyl)-8-oxo-5-thia-1-azabicyclo[4.2.0]oct-2-ene-2-carbonyl)oxy)methyl)-3-(dimethylcarbamoyl)pyridin-1-ium methane sulfonate;
xxv. L(S)-1-((2-(carboxymethyl)-4-methylpentylcarbamoyloxy)methyl)-3-(dimethylcarbamoyl)pyridinium methanesulfonate;
xxvi. (S)-1-(carboxymethyl)-4-methylpentylcarbamoyloxy)methyl)-3-(dimethylcarbamoyl)pyridinium iodide;
xxvii. 1-((2-((E)-1-(2-aminothiazol-4-yl)-2-((1S,8R)-5-(((3-(dimethylcarbamoyl)pyridinium-1 -yl)methoxy)carbonyl)-7-oxo-4-vinyl-2-thiabicyclo[4.2.0]oct-4-en 8-ylamino)-2-oxoethylideneaminooxy)acetoxy)methyl)-3-(dimethylcarbamoyl)pyridinium;
xxviii. 1-((2-((E)-1-(2-aminothiazol-4-yl)-2-((1S,8R)-5-(((3 -(dimethylcarbamoyl)pyridinium-1-yl)methoxy)carbonyl)-7-oxo-4-vinyl-2-thiabicyclo[4.2.0]oct-4-en-8-ylamino)-2-oxoethylideneaminooxy)acetoxy)methyl)-3-(dimethylcarbamoyl) pyridinium;
xxix. 1-((4-((E)-2-((6R,7R)-2-carboxy-8-oxo-3-vinyl-5-thia-1-azabicyclo[4.2.0]oct-2-en-7-ylamino)-1-(carboxymethoxyimino)-2-oxoethypthiazol-2-ylcarbamoyloxy)methyl)-3-(dimethylcarbamoyl)pyridinium;
xxx. 1-((((2,6-diisopropylphenoxy)carbonyl)oxy)methyl)-3-(dimethylcarbamoyl)pyridin-1-ium iodide;
xxxi. 3-carbamoyl-1-(((((2,6-diisopropyl-phenoxy)carbonyl)oxy)methyl)pyridin-1-ium iodide;
xxxii. 1-(((isopropylcarbamoyl)oxy)methyl)-3-(2-((2-methyl-5-((3-(4-methyl-1H-imidazol-3-ium-1-yl)-5-(trifluoromethyl)phenyl)carbamoyl)phenyl)amino)pyrimidin-4-yl)pyridin-1-ium methanesulfonate;
xxxiii. 1-(((isopropoxycarbonyl)oxy)methyl)-3-(2-((2-methyl-5-((3-(4-methyl-1H-imidazol-3-ium-1-yl)-5-(trifluoromethyl)phenyl)carbamoyl)phenyl)amino)pyrimidin-4-yl)pyridin-1-ium methanesulfonate;
xxxiv. 3-(2-((2-methyl-5-((3-(4-methyl-1H-imidazol-3-ium-1-yl)-5-(trifluoromethyl)phenyl)carbamoyl)phenyl)amino)pyrimidin-4-yl)-1-((2-phenylacetoxy)methyl)pyridin-1-ium methanesulfonate;
xxxv. 1-((isobutyryloxy)methyl)-3-(2-((2-methyl-5-((3-(4-methyl-1H-imidazol-3-ium-1-yl)-5-(trifluoromethyl)phenyl)carbamoyl)phenyl)amino)pyrimidin-4-yl)pyridin-1-ium methanesulfonate;
xxxvi. 4-((4-ethoxy-3-(1-methyl-7-oxo-3-propyl-4,7-dihydro-1H-pyrazolo[4,3-d]pyrimidin-5-yl)phenyl)sulfonyl)-1-((isobutyryloxy)methyl)-1-methylpiperazin-1-ium iodide;
xxxvii. 4-((4-ethoxy-3-(1-methyl-7-oxo-3-propyl-4,7-dihydro-1H-pyrazolo[4,3-d]pyrimidin-5-yl)phenyl)sulfonyl)-1-((isobutyryloxy)methyl)-1-methylpiperazin-1-ium methanesulfonate;
xxxviii. 4-((4-ethoxy-3-(1-methyl-7-oxo-3-propyl-4,7-dihydro-1H-pyrazolo[4,3-d]pyrimidin-5 -yl)phenyl)sulfonyl)-1-(((isopropoxycarbonyl)oxy)methyl)-1-methylpiperazin-1-ium iodide;
xxxix. 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropoxycarbonyl)oxy)methyl)-1-methylpiperazim-1-ium methanesulfonate;

xl. 1-(acetoxymethyl)-4-((4-ethoxy-3-(1-methyl-7-oxo-3-propyl-4,7-dihydro-1H-pyrazolo[4,3-d]pyrimidin-5-yl)phenyl)sulfonyl)-1-methylpiperazin-1-ium iodide;

xli. 1-(acetoxymethyl)-4-((4-ethoxy-3-(1-methyl-1-oxo-3-propyl-4,7-dihydro- 1H-pyrazolo[4,3-d]pyrimidin-5-yl)phenyl)sulfonyl)-1-methylpiperazin-1-ium methanesulfonate;

xlii. 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropylcarbamoyl)oxy)methyl)-1-methylpiperazin-1-ium methanesulfonate;

xliii. 4-((4-ethoxy-3-(1-methyl-7-oxo-3-propyl-4,7-dihydro-1H-pyrazolo[4,3-d]pyrimidin-5-yl)phenyl)sulfonyl)-1-(((isopropylcarbamoyl)oxy)methyl)-1-methylpiperazin-1-ium iodide;

xliv. (S)-1-((((2-(carboxymethyl)-4-methylpentyl)carbamoyl)oxy)methyl)-3-(methylcarbamoyl)pyridin-1-ium methanesulfonate;

xlv. (S)-3-carbamoyl-1-(((2-(carboxymethyl)-4-methylpentyl)carbamoyl)oxy)methyl)pyridin-1-ium methanesulfonate;

xlvi. (S)-1-(((3-(aminomethyl)-5-methy1H-exanoyl)oxy)methyl)-3-(dimethylcarbamoyl)pyridin-1-ium methanesulfonate;

xlvii. (S)-1-(((3-(aminomethyl)-5-methy1H-exanoyl)oxy)methyl)-3-(methylcarbamoyl)pyridin-1-ium methanesulfonate;

xlviii. (S)-1-(((3-(aminomethyl)-5-methy1H-exanoyl)oxy)methyl)-3-carbamoylpyridin-1-ium methanesulfonate;

xlix. 3-(dimethylcarbamoyl)-1-((((4-((1E,4Z,6E)-5-hydroxy-7-(4-hydroxy-3-methoxyphenyl)-3-oxohepta-1,4,6-trien-1-yl)-2-methoxyphenoxy)carbonyl)oxy)methyl)pyridin-1-ium methanesulfonate;

l. 1-(((((4-((1E,4Z,6E)-5-hydroxy-7-(4-hydroxy-3-methoxyphenyl)-3-oxohepta-1,4,6-trien-1-yl)-2-methoxyphenoxy)carbonyl)oxy)methyl)-3-(methylcarbamoyl)pyridin-1-ium methanesulfonate;

li. 3-carbamoyl-1-((((4-((1E,4Z,6E)-5-hydroxy-7-(4-hydroxy-3-methoxyphenyl)-3-oxohepta-1,4,6-trien-1-yl)-2-methoxy-phenoxy)carbonyl)oxy)methyl)pyridin-1-ium methanesulfonate;

lii. 3-(dimethylcarbamoyl)-1-((((1-phenylpropan-2-yl)carbamoyl)oxy)methyl)pyridin-1-ium methanesulfonate;

liii. 1-((((1-carboxy-2-(3,4-dihydroxyphenyl)ethyl)carbamoyl)oxy)methyl)-3-(dimethylcarbamoyl)pyridin-1-ium methanesulfonate;

liv. 1-((((1-carboxy-2-(3,4-dihydroxyphenyl)ethyl)carbamoyl)oxy)methyl)-3-(methylcarbamoyl)pyridin-1-ium methanesulfonate:

lv. 3-carbamoyl-1-((((1-carboxy-2-(3,4-dihydroxyphenyl)ethyl)carbamoyl)oxy)methyl)pyridin-1-ium methanesulfonate;

lvi. 1-((((3,4-dihydroxyphenethyl)carbamoyl)oxy)methyl)-3-(dimethylcarbamoyl)pyridin-1-ium methanesulfonate;

lvii. 1-((((3,4-dihydroxyphenethyl)carbamoyl)oxy)methyl)-3-(methylcarbamoyl)pyridin-1-ium methanesulfonate;

lviii. 3-carbamoyl-1-(((3,4-dihydroxy-phenethyl)carbamoyl)oxy)methyl)pyridin-1-ium methanesulfonate;

lix. 1-((((4-acetamidophenoxy)carbonyl)oxy)methyl)-3-(dimethylcarbamoyl)pyridin-1-ium mesylate;

lx. 1-(((2,6-diisopropylphenoxy)carbonyl)oxy)methyl)-3-(methoxycarbonyl)pyridin-1-ium iodide;

lxi. 3-carboxy-1-((((2,6-diisopropylphenoxy)carbonyl)oxy)methyl)pyridin-1-ium iodide;

lxii. 2-4(2,6-diisopropylphenoxy)carbonyl)oxy)-N,N,N-trimethylethan-1-aminium iodide;

lxiii. 2-4(2,6-diisopropylphenoxy)carbonyl)oxy)-N,N-dimethylethan-1-aminium chloride;

lxiv. 1-((((2,6-diisopropylphenoxy)carbonyl)oxy)methyl)-3-(hydroxycarbamoyl)pyridin-1- ium iodide;

lxv. 3-(((((2,6-diisopropylphenoxy)carbonyl)oxy)methyl)carbamoyl)-1-methylpyridin-1-ium iodide;

lxvi. 1-4(2,6-diisopropylphenoxy)carbonyl)oxy)-N-((((2,6-diisopropylphenoxy)carbonyl)oxy)methyl)-N,N-dimethyl-methanaminium iodide;

lxvii. 2-4(2,6-diisopropylphenoxy)carbonyl)oxy)-N-((((2,6-diisopropylphenoxy)carbonyl)oxy)methyl)-N,N-dimethylethan-1-aminium iodide;

lxviii. 1-((((2,6-diisopropylphenoxy)carbonyl)oxy)methyl)-4-formyl-3-hydroxy-5-(hydroxymethyl)-2-methylpyridin-1-ium iodide;

lxix. 3-((2,6-diisopropylphenoxy)carbonyl)-1-((((2,6-diisopropylphenoxy)carbonyl)oxy)methyl)pyridin-1-ium methanesulfonate;

lxx. 2-4(2,6-diisopropylphenoxy)carbonyl)oxy)-N,N,N-trimethylethan-1-aminium methanesulfonate;

lxxi. 1-(((11-cyclopropyl-4-methyl-6-oxo-6,11-dihydro[3,2-b:2',3'-e][1,4]diazepine-5-carbonyl)oxy)methyl)-3-(methylcarbamoyl)pyridin-1-ium methanesulfonate;

lxxii. 1-(((11-cyclopropyl-4-methyl-6-oxo-6,11-dihydro-5H-dipyrido[3,2-b:2',3'-e][1,4]diazepine-5-carbonyl)oxy)methyl)-3-(dimethylcarbamoyl)pyridin-1-ium methanesulfonate;

lxxiii. 3-carbamoyl-1-(((11-cyclopropyl-4-methyl-6-oxo-6,11-dihydro-5H-dipyrido[3,2-b:2',3'-e][1,4]diazepine-5-carbonyl)oxy)methyl)pyridin-1-ium methanesulfonate;

lxxiv. 3-(dimethylcarbamoyl)-1-((2-(4-isobutylphenyl)propanoyloxy)methyl)pyridinium mesylate;

lxxv. (S)-1-((((2-(carboxymethyl)-2,4-dimethylpentyl)carbamoyl)oxy)methyl)-3-(dimethylcarbamoyl)pyridin-1-ium iodide;

lxxvi. (S)-1-(((2-(carboxymethyl)-2,4-dimethylpentyl)carbamoyl)oxy)methyl)-3-(dimethylcarbamoyl)pyridin-1-ium methanesulfonate;

lxxvii. 3-carbamoyl-1-(((((2,6-diisopropylphenoxy)carbonyl)oxy)methyl)pyridin-1-ium bromide;

lxxviii. 3-carbamoyl-1-((((2,6-diisopropylphenoxy)carbonyl)oxy)methyl)pyridin-1-ium chloride;

lxxix. 1-((((2,6-diisopropylphenoxy)carbonyl)oxy)methyl)-3-(methylcarbamoyl)pyridin-1- ium tetrafluoroborate;

lxxx. 1-((((2,6-diisopropylphenoxy)carbonyl)oxy)methyl)-3-(methylcarbamoyl)pyridin-1-ium nitrate;

lxxxi. 1-((((2,6-diisopropylphenoxy)carbonyl)oxy)methyl)-3-(methylcarbamoyl)pyridin-1-ium chloride;

lxxxii. 1-((((2,6-diisopropylphenoxy)carbonyl)oxy)methyl)-3-(methoxycarbonyl)pyridin-1- ium methanesulfonate; and lxxxiii. 3-carboxy-1-(((2,6-diisopropylphenoxy)carbonyl)oxy)methyl)pyridin-1-ium methanesulfonate.

3. The method of claim 2, wherein the modified drug compound is selected from the group consisting of:

i. 1-((((2,6-diisopropylphenoxy)carbonyl)oxy)methyl)-3-(dimethylcarbamoyl)pyridin-1-ium methanesulfonate ii. 1-((((2,6-diisopropylphenoxy)carbonyl)oxy)methyl)-3-(methylcarbamoyl)pyridin-1-ium iodide iii. 3-carbamoyl-1-((((2,6-diisopropylphenoxy)carbonyl)oxy)methyl)pyridin-1-ium iodide
iv. 1-((((2,6-diisopropylphenoxy)carbonyl)oxy)methyl)-3-(methoxycarbonyl)pyridin-1-ium iodide
v. 3 carboxy-1-((((2,6-diisopropylphenoxy)carbonyl)oxy)methyl)pyridin-1-ium iodide
vi. 3-((2,6-diisopropylphenoxy)carbonyl)-1-methylpyridin-1-ium iodide
vii. 2,6-diisopropylphenyl nicotinate hydrochloride
viii. 3-((2,6-diisopropylphenoxy)carbonyl)-1-(((isopropylcarbamoyl)oxy)methyl)pyridin-1-ium methanesulfonate
ix. 3-((2,6-diisopropylphenoxy)carbonyl)-1-((((2,6-diisopropylphenoxy)carbonyl)oxy)methyl)pyridin-1-ium iodide
x. 2-4(2,6-diisopropylphenoxy)carbonyl)oxy)-N,N,N-trimethylethan-1-aminium iodide
xi. 2-4(2,6-diisopropylphenoxy)carbonyl)oxy)-N,N-dimethylethan-1-aminium chloride
xii 1-(((2,6-diisopropylphenoxy)carbonyl)oxy)methyl)-3-(hydroxycarbamoyl)pyridin-1-ium iodide;
xiii. 3-(((((2,6-diisopropylphenoxy)carbonyl)oxy)methyl)carbamoyl)-1-methylpyridin-1-ium iodide
xiv. 1-(((2,6-diisopropylphenoxy)carbonyl)oxy)-N-(((2,6-diisopropylphenoxy)carbonyl)oxy)methyl)-N,N-dimethylmethanaminium iodide
xv. 2-4(2,6-diisopropylphenoxy)carbonyl)oxy)-N-((((2,6-diisopropylphenoxy)carbonyl)oxy)methyl)-N,N-dimethylethan-1-aminium iodide; and
xvi. 1-((((2,6-diisopropylphenoxy)carbonyl)oxy)methyl)-4-formyl-3-hydroxy-5-(hydroxymethyl)-2-methylpyridin-1-ium iodide.

4. The method of claim 1, wherein the modified drug compound is present as its stereoisomer or mixture of stereoisomers.

* * * * *